US010702481B2

(12) United States Patent
Myerson et al.

(10) Patent No.: US 10,702,481 B2
(45) Date of Patent: Jul. 7, 2020

(54) SYSTEMS AND METHODS FOR THE FABRICATION OF TABLETS, INCLUDING PHARMACEUTICAL TABLETS

(71) Applicant: Massachusetts Institute of Technology, Cambridge, MA (US)

(72) Inventors: Allan S. Myerson, Boston, MA (US); Mohammad A. Azad, Quincy, MA (US); Gregory J. Hammersmith, Windsor, CT (US); David Brancazio, Cambridge, MA (US); Juan Guillermo Osorio Caicedo, Elizabeth, NJ (US)

(73) Assignee: Massachusetts Institute of Technology, Cambridge, MA (US)

( * ) Notice: Subject to any disclaimer, the term of this patent is extended or adjusted under 35 U.S.C. 154(b) by 203 days.

(21) Appl. No.: 15/898,010

(22) Filed: Feb. 15, 2018

(65) Prior Publication Data
US 2018/0271791 A1 Sep. 27, 2018

Related U.S. Application Data

(60) Provisional application No. 62/460,626, filed on Feb. 17, 2017, provisional application No. 62/619,638, (Continued)

(51) Int. Cl.
*A61K 9/20* (2006.01)
*A61J 3/10* (2006.01)
(Continued)

(52) U.S. Cl.
CPC ............... *A61K 9/2095* (2013.01); *A61J 3/10* (2013.01); *A61K 9/2009* (2013.01);
(Continued)

(58) Field of Classification Search
None
See application file for complete search history.

(56) References Cited

U.S. PATENT DOCUMENTS 2,421,714 A 6/1947 Rieveschl
2,441,498 A 5/1948 Lofgren et al.
(Continued)

FOREIGN PATENT DOCUMENTS

EP 2374534 A1 10/2011
EP 2427166 B1 10/2013
WO WO 2016/025803 A1 2/2016

OTHER PUBLICATIONS

Extended European Search Report dated Mar. 5, 2018 for Application No. EP 15832380.8.
(Continued)

*Primary Examiner* — Mary Lynn F Theisen
(74) *Attorney, Agent, or Firm* — Wolf, Greenfield & Sacks, P.C.

(57) ABSTRACT

Systems and methods for fabricating ingestible pharmaceutical tablets are provided. Certain of the systems and methods described herein are capable of manufacturing tablets of different dosages without the need to fluidically connect or disconnect unit operations when switching from a tablet having a first dosage to a tablet having a second, different dosage. Certain of the systems and methods described herein are capable of manufacturing compositionally tablets, e.g., tablets with different active pharmaceutical ingredients (APIs).

29 Claims, 31 Drawing Sheets

Related U.S. Application Data filed on Jan. 19, 2018, provisional application No. 62/621,429, filed on Jan. 24, 2018.

(51) Int. Cl.

| | | |
|---|---|---|
| *B01F 13/10* | (2006.01) | |
| *B30B 15/30* | (2006.01) | |
| *B30B 11/02* | (2006.01) | |
| *B30B 11/08* | (2006.01) | |
| *B29C 43/34* | (2006.01) | |
| *A61K 31/192* | (2006.01) | |
| *A61K 31/5513* | (2006.01) | |

(52) U.S. Cl.
CPC .......... *A61K 9/2013* (2013.01); *A61K 9/2018* (2013.01); *A61K 31/192* (2013.01); *A61K 31/5513* (2013.01); *B01F 13/1061* (2013.01); *B01F 13/1063* (2013.01); *B29C 43/34* (2013.01); *B30B 11/027* (2013.01); *B30B 11/08* (2013.01); *B30B 15/302* (2013.01)

(56) References Cited

U.S. PATENT DOCUMENTS

| | | | |
|---|---|---|---|
| 5,925,732 | A | 7/1999 | Ecker et al. |
| 6,782,307 | B2* | 8/2004 | Wilmott ................ A61K 8/044 700/233 |
| 6,806,087 | B2 | 10/2004 | Kibby et al. |
| 7,172,735 | B1 | 2/2007 | Lowe et al. |
| 7,241,423 | B2 | 7/2007 | Golbig et al. |
| 7,790,124 | B2 | 9/2010 | Matteo |
| 7,854,902 | B2 | 12/2010 | Matteo |
| 8,426,630 | B2 | 4/2013 | McQuade et al. |
| 8,540,939 | B2 | 9/2013 | Niesz et al. |
| 8,584,349 | B2 | 11/2013 | Scannon et al. |
| 9,440,381 | B1* | 9/2016 | Shaham ................ B29C 43/36 |
| 2004/0028765 | A1 | 2/2004 | Kerzner et al. |
| 2004/0063992 | A1 | 4/2004 | Chiang et al. |
| 2004/0172169 | A1 | 9/2004 | Wright, IV et al. |
| 2005/0042149 | A1 | 2/2005 | Bard |
| 2005/0175519 | A1 | 8/2005 | Rogers, Jr. et al. |
| 2005/0177280 | A1 | 8/2005 | Almstetter et al. |
| 2007/0144967 | A1 | 6/2007 | Guenther et al. |
| 2007/0148211 | A1* | 6/2007 | Altreuter .............. A61K 9/0056 424/441 |
| 2008/0047972 | A1* | 2/2008 | Bartholomew ...... A45D 44/005 222/1 |
| 2008/0233018 | A1 | 9/2008 | Van Dam et al. |
| 2008/0233653 | A1 | 9/2008 | Hess et al. |
| 2009/0043141 | A1 | 2/2009 | Mazanec et al. |
| 2009/0282978 | A1 | 11/2009 | Jensen et al. |
| 2010/0285575 | A1 | 11/2010 | Michiels |
| 2010/0324157 | A1 | 12/2010 | Bauman et al. |
| 2011/0104043 | A1 | 5/2011 | Niesz et al. |
| 2011/0132822 | A1 | 6/2011 | Kaw |
| 2011/0258837 | A1 | 10/2011 | Scannon et al. |
| 2012/0061869 | A1 | 3/2012 | Boeckx et al. |
| 2012/0107175 | A1 | 5/2012 | Satyamurthy et al. |
| 2012/0325469 | A1 | 12/2012 | Olson et al. |
| 2013/0260419 | A1 | 10/2013 | Ransohoff et al. |
| 2013/0334247 | A1 | 12/2013 | Lee et al. |
| 2015/0291411 | A1 | 10/2015 | Ittstein |
| 2015/0374586 | A1* | 12/2015 | Gamlen ................ B30B 15/026 425/150 |
| 2016/0243781 | A1* | 8/2016 | Vandenbroucke ...... B30B 11/08 |
| 2017/0282420 | A1* | 10/2017 | Kitamura .......... B01F 15/00207 |
| 2018/0304569 | A1* | 10/2018 | Gamlen ................... A61J 3/10 |

OTHER PUBLICATIONS

International Search Report and Written Opinion for PCT/US2015/045220 dated Nov. 24, 2015.
International Preliminary Report on Patentability dated Mar. 2, 2017 for Application No. PCT/US2015/045220.
[No Author Listed], Defense Advanced Research Project Agency (DARPA), Broad Agency Announcement, Pharmacy on Demand (PoD), Defense Sciences Office (DSO), DARPA-BAA-11-05. Oct. 21, 2010;1-41.
[No Author Listed], WHO Model List of Essential Medicines, 18$^{th}$ List, Apr. 2013, 47 pages. http://www.who.int/medicines/publications/essentialmedicines/en/index.html (accessed Aug. 3, 2013).
[No Author Listed], CDC, 2017. Centers for Disease Control and Prevention (CDC)—Strategic National Stockpile. https://www.cdc.gov/phpr/stockpile/index.htm. Nov. 12, 2017 capture, the WayBack Machine, https://web.archive.org/web/20171112100749/https://www.cdc.gov/phpr/stockpile/index.htm. 7 pages.
[No Author Listed], Strategic Plan for Preventing and Mitigating Drug Shortages—Food and Drug Administration. 40 pages. Oct. 2013.
[No Author Listed], FDA, 2017. Developing Products for Rare Diseases and Conditions. https://www.fda.gov/ForIndustry/DevelopingProductsforRareDiseasesConditions/default.htm. Feb. 21, 2017 capture, the WayBack Machine, https://web.archive.org/web/20170221130110.https://www.fda.gov/ForIndustry/Developing . . . 2 pages.
Abboud et al., Factory shift: new prescription for drug makers: update the plants; after years of neglect, industry focuses on manufacturing; FDA acts as a catalyst; the three-story blender. Wall Street J. Sep. 3, 2003, 5 pages.
Abdullah et al., The use of bulk density measurements as flowability indicators. Powder Technol. Mar. 1999; 102(2):151-65.
Adamo et al., On-demand continuous-flow production of pharmaceuticals in a compact, reconfigurable system. Science. Apr. 1, 2016;352(6281):61-7.
Ahmed-Omer et al., Preparation of fluoxetine by multiple flow processing steps. Org Biomol Chem. May 21, 2011;9(10):3854-62. doi:10.1039/c0ob00906g. Epub Mar. 30, 2011.
Amidon et al., Particle, powder, and compact characterization. Originally published in Ch. 8 in Developing Solid Oral Dosage Forms: Pharmaceutical Theory and Practice. Jan. 2009, pp. 163-186. Academic Press. New York. Republished as Ch 10 in Developing Solid Oral Dosage Forms: Pharmaceutical Theory and Practice. Second Edition. 2017;271-93. Epub Nov. 2016.
Anderson, Using continuous processes to increase production. Org Process Res Dev. Feb. 2012;16(5):852-69.
Benyahia et al., A plant-wide dynamic model of a continuous pharmaceutical process. Ind Eng Chem Res. Oct. 2012; 51(47):15393-412.
Bogdan et al., the continuous-flow synthesis of ibuprofen. Angew Chem Int Ed Engl. 2009;48(45):8547-50. doi: 10.1002/anie.200903055.
Freeman, Measuring the flow properties of consolidated, conditioned and aerated powders—A comparative study using a powder rheometer and a rotational shear cell. Powder Technol. May 2007; 174(1):25-33. Epub Oct. 24, 2006.
Han et al., Dry coating of micronized API powders for improved dissolution of directly compacted tablets with high drug loading. Int J Pharm. Feb. 14, 2013;442(1-2):74-85. doi: 10.1016/j.ijpharm.2012.08.004. Epub Aug. 8, 2012.
Hartman et al., Deciding whether to go with the flow: Evaluating the merits of flow reactors for synthesis. Angew Chem Int Ed Engl. Aug. 8, 2011;50(33):7502-19. doi: 10.1002/anie.201004637. Epub Jun. 27, 2011.
Hartman et al., Microchemical systems for continuous-flow synthesis. Lab Chip. Sep. 7, 2009;9(17):2495-507. doi: 10.1039/b906343a. May 28, 2009.
Hessel, Novel process windows—gate to maximizing process intensification via flow chemistry. Chem Eng Technol. Nov. 2009;32(11):1655-81.
Hogan, A little goes a long way. Nature. Jul. 27, 2006;442:351-2. Erratum in: Nature. Jul. 27, 2006;442:351-2.
Jenike, Storage and flow of solids. Bulletin No. 123 of the Utah Engineering Experiment Station. University of Utah. vol. 53, No. 26, Nov. 1964 (6$^{th}$ printing (revised) Mar. 1970). 209 pages.

(56) References Cited

OTHER PUBLICATIONS

Jimenez-Gonzalez et al., Key green engineering research areas for sustainable manufacturing: A perspective from pharmaceutical and fine chemicals manufacturers. Org Process Res Dev. Jul. 2011; 15(4):900-11.

Katneni et al., Permeability assessment of poorly water-soluble compounds under solubilizing conditions: The reciprocal permeability approach. J Pharm Sci. Oct. 2006;95(10):2170-85.

Knieke et al., Sub-100 micron fast dissolving nanocomposite drug powders. Powder Technol. Feb. 2015;271:49-60. Epub Oct. 24, 2014.

Lewin et al., Pharmacy on demand: New technologies to enable miniaturized and mobile drug manufacturing. Am J Health Syst Pharm. Jan. 15, 2016;73(2):45-54. doi: 10.2146/ajhp150639.

Malet-Sanz, Continuous flow synthesis. A pharma perspective. J Med Chem. May 10, 2012;55(9):4062-98. doi: 10.1021/jm2006029. Epub Jan. 27, 2012.

Mason et al., Greener approaches to organic synthesis using microreactor technology. Chem Rev. Jun. 2007;107(6):2300-18. Epub Mar. 21, 2007.

McCormick, Evolutions in direct compression. Pharm Technol. Apr. 2005;17:52-62.

Monbaliu et al., Compact and integrated approach for advanced end-to-end production, purification, and aqueous formulation of lidocaine hydrochloride. Org Proc Res Dev. 2016;20(7):1347-53. Epub Jun. 21, 2016.

Newton et al., Computer analysis of the relation between tablet strength and compaction pressure. J Pharm Pharmacol. Dec. 1971;23:195S-201S.

Plumb, Continuous processing in the pharmaceutical industry—Changing the mindset. Chem Eng Res Des. Trans IChemE, Part A. Jun. 2005;83(A6):730-8.

Poechlauer et al., Continuous processing in the manufacture of active pharmaceutical ingredients and finished dosage forms: An industry perspective. Org Process Res Dev, Sep. 2012;16(10):1586-90.

Proctor et al., Continuous processing in the pharmaceutical industry, in Green Chemistry in the Pharmaceutical Industry, Ch. 11, 221-42. Wiley-VCH: Weinheim, Germany. 2010.

Razavi et al., Toward predicting tensile strength of pharmaceutical tablets by ultrasound measurement in continuous manufacturing. Int J Pharm. Jun. 30, 2016;507(1-2):83-9. doi: 10.1016/j.ijpharm.2016.04.064. Epub May 5, 2016.

Reilly, The preparation of lidocaine. J Chem Educ. Nov. 1999;76(11):1557.

Roberge et al., Microreactor technology: A revolution for the fine chemical and pharmaceutical industries? Chem Eng Technol. 2005;28(3):318-23.

Roberge et al., Microreactor technology and continuous processes in the fine chemical and pharmaceutical industry: Is the revolution underway? Org Process Res Dev. 2008;12(5):905-10. Epub Aug. 19, 2008.

Schaber et al., Economic analysis of integrated continuous and batch pharmaceutical manufacturing: A case study. Ind Eng Chem Res. Jul. 2011;50(17):10083-92.

Schulze, Powders and Bulk Solids: Behavior, Characterization, Storage and Flow. Ch. 3, Flow properties of bulk solids. pp. 35-74. 2008. Springer Verlag: Berlin Heidelberg.

Serajuddin, The future of tableting technology. J Excipients Food Chem. Mar. 2014; 5(1):1-4.

Seton et al., Compaction of recrystallized ibuprofen. Chem Eng J. Nov. 1, 2010;164(2):449-52.

Sinka et al., The effect of processing parameters on pharmaceutical tablet properties. Powder Technol. Jan. 31, 2009;189(2):276-84. Epub Apr. 18, 2008.

Snead et al., End-to-end continuous flow synthesis and purification of diphenhydramine hydrochloride featuring atom economy, in-line separation, and flow of molten ammonium salts. Chem Sci. 2013;4(7):2822-27. doi: 10.1039/c3sc50859e.

Stankiewicz et al., Process intensification: transforming chemical engineering. Chem Eng Prog. Jan. 2000;96:22-34.

Stelzer et al., Evaluation of PAT methods for potential application in small-scale, multipurpose pharmaceutical manufacturing platforms. Org Proc Res Dev. 2016;20:1431-8. Epub Jul. 15, 2016.

Sugasawa et al., A new simple synthesis of 1,4-benzodiazepines. J Heterocyclic Chem. Apr. 1979; 16(3):445-8.

Sun, Setting the bar for powder flow properties in successful high speed tableting. Powder Technol. Jul. 1, 2010;201:106-8. Epub Mar. 16, 2010.

Sun et al., Particle engineering for enabling a formulation platform suitable for manufacturing low-dose tablets by direct compression. J Pharm Sci. Jul. 1, 2017;106(7):1772-7. Epub Mar. 16, 2017.

Thomas, The reality of continuous processing. Manuf Chem. 2005 Apr. 1, accessed Jun. 21, 2017 at http://www.manufacturingchemist.com/technica/article_page/The_reality_of_continous . . . , 5 pages.

Tye et al., Evaluation of the effects of tableting speed on the relationships between compaction pressure, tablet tensile strength, and tablet solid fraction. J Pharm Sci. Mar. 2005;94(3):465-72.

Webb et al., Continuous flow multi-step organic synthesis. Chem Sci. 2010, 1, 675-80. doi: 10/1039/c0sc00381f. Epub Sep. 23, 2010.

Wegner et al., Ten key issues in modern flow chemistry. Chem Commun (Camb). Apr. 28, 2011;47(16):4583-92. doi: 10.1039/c0cc05060a. Epub Mar. 15, 2011.

Whitesides, The origins and the future of microfluidics. Nature. Jul. 27, 2006;442(7101):368-73.

Wiles et al., Micro Reaction Technology in Organic Synthesis. 453 pages (submitted in 2 parts), CRC Press: Boca Raton, 2011.

Yamauchi et al., A facile and efficient preparative method of methyl 2-arylpropanoates by treatment of propiophenones and their derivatives with iodine or iodine chlorides. J Org Chem. 1988;53(20):4858-9.

International Preliminary Report on Patentability dated Aug. 29, 2019 for Application No. PCT/US2018/018359.

Invitation to Pay Additional Fees dated May 16, 2018 for Application No. PCT/US2018/018359.

International Search Report and Written Opinion dated Jul. 19, 2018 for Application No. PCT/US2018/018359.

\* cited by examiner

| Materials | Trade name | Run# | Start amount | Powder remains on boat | |
|---|---|---|---|---|---|
| | | | gm | gm | % |
| Silicified MCC | Prosolv HD90 | 1 | 1.4691 | 0.0167 | 1.137 |
| | | 2 | 1.511 | 0.0134 | 0.887 |
| | | 3 | 1.5639 | 0.015 | 0.959 |
| | | 4 | 1.4817 | 0.0103 | 0.695 |

FIG. 11

SYSTEMS AND METHODS FOR THE FABRICATION OF TABLETS, INCLUDING PHARMACEUTICAL TABLETS

CROSS-REFERENCE TO RELATED APPLICATIONS

This Application claims the benefit under 35 U.S.C. § 119(e) of U.S. Provisional Application Ser. No. 62/460,626, entitled "SYSTEMS AND METHODS FOR THE FABRICATION OF TABLETS, INCLUDING PHARMACEUTICAL TABLETS" filed on Feb. 17, 2017, and U.S. Provisional Application Ser. No. 62/619,638, entitled "SYSTEMS AND METHODS FOR THE FABRICATION OF TABLETS, INCLUDING PHARMACEUTICAL TABLETS" filed on Jan. 19, 2018, and U.S. Provisional Application Ser. No. 62/621,429, "SYSTEMS AND METHODS FOR THE FABRICATION OF TABLETS, INCLUDING PHARMACEUTICAL TABLETS" filed on Jan. 24, 2018, the entire contents of each of which are incorporated herein by reference.

GOVERNMENT SPONSORSHIP

This invention was made with Government support under Contract No. N66001-11-C-4147 awarded by the Space and Naval Warfare Systems Center. The Government has certain rights in the invention.

TECHNICAL FIELD

Systems and methods for fabricating tablets, including pharmaceutical tablets, are generally described.

BACKGROUND

Recently, pharmaceutical and biotechnology industries have experienced periods of slowed growth and increased costs associated with the development of new pharmaceutical products. While individual processes involved in certain pharmaceutical manufacturing are transitioning to continuous-like processes, pharmaceutical facilities generally still rely on batch or semi-batch techniques to produce complex chemical products. Current processes are typically tailored to manufacture a single specific type of pharmaceutical tablet and generally require large, expensive, and static setups. While continuous processes are suggested to offer numerous benefits, including reduced cost, complete infrastructure and systems capable of complex continuous manufacturing of pharmaceutical tablets do not exist. The ability to fabricate pharmaceutical tablets (and, in some cases, compositionally different types of pharmaceutical tablets) in a single self-contained system remains elusive.

SUMMARY

Systems and methods for fabricating tablets, including pharmaceutical tablets, are provided. Certain of the systems and methods described herein are capable of manufacturing tablets of different dosages without the need to fluidically connect or disconnect unit operations when switching from a tablet having a first dosage to a tablet having a second, different dosage. Certain of the systems and methods described herein are capable of manufacturing compositionally tablets, e.g., tablets with different active pharmaceutical ingredients (APIs). The subject matter of the present invention involves, in some cases, interrelated products, alternative solutions to particular problem, and/or a plurality of different uses of one or more systems and/or articles.

According to one aspect, a method for producing an ingestible pharmaceutical composition is provided. The method can comprise, in some embodiments, receiving, with a controller, instructions regarding a first tablet dosage and a second tablet dosage. The method may also include dispensing a first amount of a solid active pharmaceutical ingredient and dispensing a first amount of an excipient. The method may also include blending the first amount of the solid active pharmaceutical ingredient and the first amount of the excipient to form a first mixture having a volume of less than 10 L. The method may also include forming a first tablet from the first mixture, dispensing a second amount of the solid active pharmaceutical ingredient and dispensing a second amount of the excipient. The method may also include blending the second amount of the solid active pharmaceutical ingredient and the second amount of the excipient to form a second mixture and forming a second tablet from the second mixture, wherein a dosage of the active pharmaceutical ingredient of the first tablet is different from a dosage of the active pharmaceutical ingredient of the second tablet.

According to another aspect, a method of producing an ingestible pharmaceutical composition is provided. The method can comprise, in some embodiments, receiving, with a controller, instructions regarding a first tablet dosage and a second tablet dosage. The method may also include providing a first dispenser, a second dispenser, a blender and a frame, wherein the first dispenser, the second dispenser and the blender are coupled to the frame. The method may also include dispensing a first amount of a solid active pharmaceutical ingredient, dispensing a first amount of an excipient, and blending the first amount of the solid active pharmaceutical ingredient and the first amount of the excipient to form a first mixture, and forming a first tablet from the first mixture. The method may also include dispensing a second amount of the solid active pharmaceutical ingredient, dispensing a second amount of the excipient, blending the second amount of the solid active pharmaceutical ingredient and the second amount of the excipient to form a second mixture and forming a second tablet from the second mixture.

According to yet another aspect, a method of producing an ingestible pharmaceutical composition is provided. The method can comprise, in some embodiments, receiving, with a controller, instructions regarding a first drug type and a second drug type. The method may also include dispensing a first solid active pharmaceutical ingredient, dispensing a first excipient, blending the first solid active pharmaceutical ingredient and the first excipient to form a first mixture having a volume of less than 10 L, and forming a tablet from the first mixture. The method may also include dispensing a second solid active pharmaceutical ingredient, the second solid active pharmaceutical ingredient being compositionally different from the first solid active pharmaceutical ingredient, dispensing a second excipient, blending the second solid active pharmaceutical ingredient and the second excipient to form a second mixture, and forming a tablet from the second mixture.

According to yet another aspect, a system for producing an ingestible pharmaceutical composition is provided. The system can comprise, in some embodiments, a plurality of dispensers, a first weigh scale configured to weigh material dispensed from the plurality of dispensers, and a blender configured to receive and mix the material dispensed from the plurality of dispensers to form a first mixture, the blender having a volume of less than 10 L.

According to yet another aspect, a system for producing an ingestible pharmaceutical composition is provided. The system can comprise, in some embodiments, a frame, a plurality of dispensers, a weigh scale configured to weigh material dispensed from the plurality of dispensers, and a blender configured to receive and mix the material dispensed from the plurality of dispensers to form a first mixture, wherein the plurality of dispensers, the weigh scale and the blender are coupled to the frame.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 11 depicts a chart indicating carrying unit performance;

DETAILED DESCRIPTION

Figure 1:
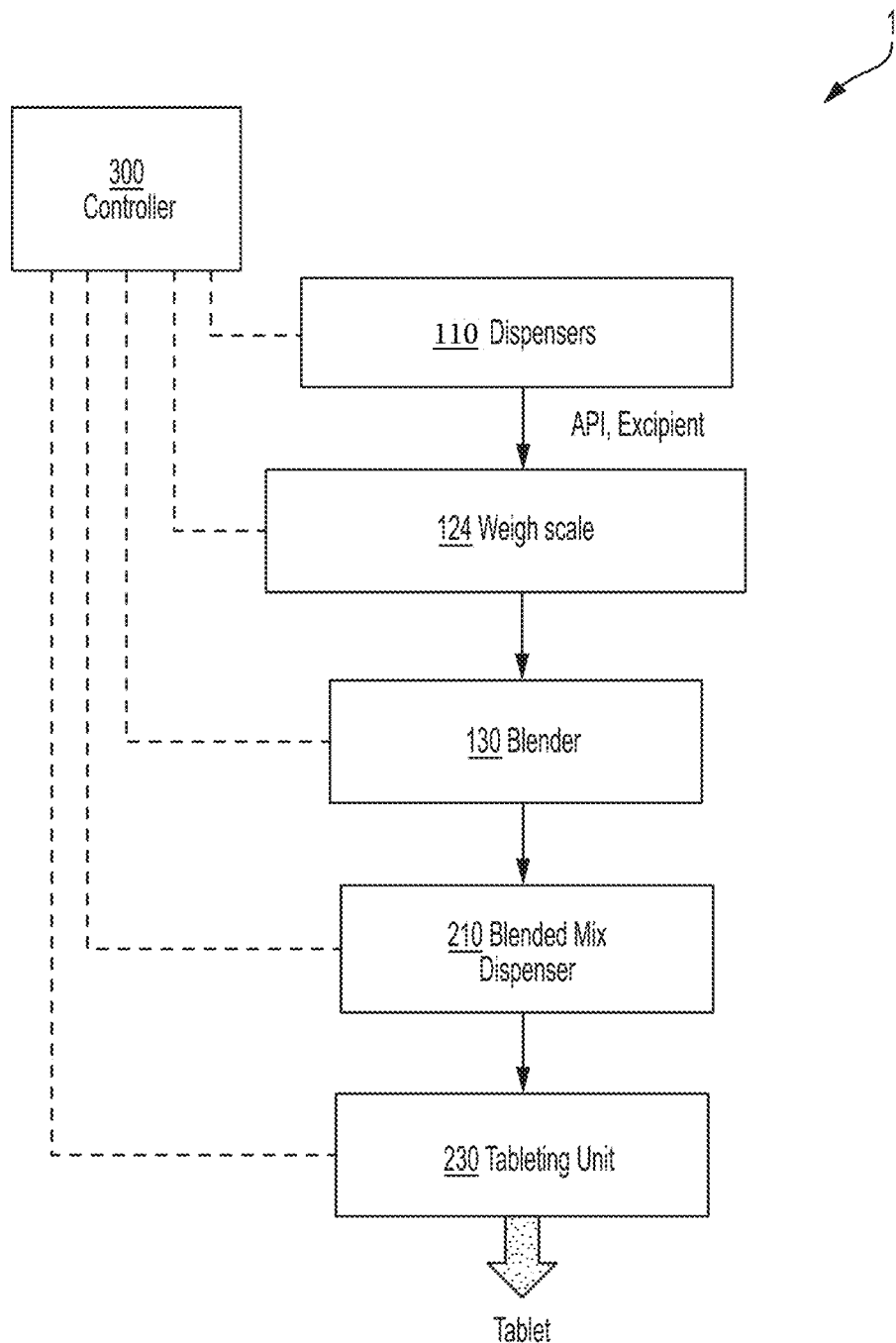
FIG. 1 is a schematic illustration of a system for producing pharmaceutical tablets according to one set of embodiments.

Systems and methods related to fabricating tablets, including pharmaceutical tablets, are generally described.

The ability to fabricate pharmaceutical tablets in a portable, self-contained, and/or readily reconfigurable system remains generally elusive. In the pharmaceutical industry, pharmaceutical tablets are typically made from large formulated blend batches on the scale of kilos to tons. Such processes require a large investment in equipment, space and materials. Also, with substantial expense tied to each batch, substantial financial losses are associated with the loss of a batch due to quality problems. With high production volumes, a longer shelf-life of several years or months may be required. As a result, comprehensive and rigorous final product testing must be conducted to measure shelf life/stability (active pharmaceutical ingredient degradability, sensitivity to temperature and moisture, etc.). Coatings are sometimes needed to prolong shelf life of mass-produced tablets. Developing suitable coating formulations can be a significant challenge, as coatings introduce potential issues such as adherence, cracking, degree of moisture protection, effect on dissolution rate and compatibility with active pharmaceutical ingredients (APIs) and excipients. Such considerations may limit the choice of acceptable APIs and/or excipients. When shelf-life is of concern, additional testing may be required. Packaging appropriate to sustain a long shelf-life may be designed and tested. This can introduce additional compatibility concerns (e.g., between the packaging and the coating material). High production volumes can also come with the downside of high expense and down-time associated with any product changes. It may therefore be difficult, for example, for typical pharmaceutical facilities to be flexible to customer demand, or to accommodate market demand for "orphan" drugs.

Described herein is a system and method for making pharmaceutical, finished dosage form tablets. The unit may provide various benefits over conventional batch processes. The inventors have appreciated that, in some cases, the unit may provide various benefits; for example, it may: (1) help address regional drug shortages, (2) provide a solution for drugs with a short shelf life, (3) be reconfigurable to produce multiple drug products, (4) be located at locations where drug products are required, (5) be put into immediate production of drugs based on demand, bypassing the need to stockpile drugs, and/or (6) reduce formulation complexity relative to products needing yearlong stability.

According to one aspect, the system is a compact, portable unit. In some embodiments, the system holds and processes volumes of material that are much smaller than those of traditional batch processes. In some embodiments, multiple components of the system are coupled together to a common frame, as opposed to having large components independent of one another spread out over a facility floor.

According to one aspect, the method involves using a system to fabricate a first tablet and a second tablet, the two tablets being different from one another. In some embodiments, the two tablets may include the same API, but be of different dosages. In some cases, the system may automatically switch between production of the two different dosages without any physical changes to the system components. In some embodiments, the first tablet may include an API that is compositionally different from the API of the second tablet. In some cases, touch points in the system, i.e., components of the system that come into contact with API, may be substituted with clean components when the system switches from producing tablets that include one API to producing tablets that include a compositionally different API.

According to one aspect, the tablets may be created on-demand, e.g., a user may input an instruction to the system specifying the desired dosage and/or desired API of the tablet. In some embodiments, a user may specify the number of desired tablets. In response, the system will dispense the appropriate type and amount of API and excipient to form a blended mix for the tablet in accordance with the user's instruction. In some embodiments, the system includes a controller that receives the user's instruction and controls the system components to carry out steps in accordance with the instruction.

In one set of embodiments, systems and methods related to producing one or more pharmaceutical tablets are described. FIG. 1 depicts a schematic illustration of system 1 according to one set of embodiments, which can be used to produce one or more pharmaceutical tablets. In some embodiments, the system comprises one or more modules. Each module can contain at least one unit operation. The unit operation can be used to perform a step of a tablet fabrication process.

In some embodiments, the system comprises a plurality of modules that interact with one another. For example, in certain embodiments, the system comprises multiple modules that interact with one another. In some such embodiments, each of the modules within the system can be used to perform one or more steps of a multi-step tablet production process.

Referring to FIG. 1, for example, system 1 comprises modules 110, 124, 130, 210 and 230. In some embodiments, module 110 comprises a plurality of dispensers, module 124 comprises a weigh scale, module 130 comprises a blender, module 210 comprises a dispenser, and module 230 comprises a tableting unit. Dispensers 110 can be used to dispense tablet materials, and a weigh scale 124 can be used to weigh the dispensed material, a blender 130 can be used to mix the dispensed materials, a blended mix dispenser 210 can be used to dispense the blended mix, and a tableting unit 230 can be used to form a tablet 2 from the blended mix. In some embodiments, material dispensed from the dispensers 110 is conveyed to the blender 130. According to one aspect, the weighing function and conveying function may be integrated into one material carrying unit. In some embodiments, a controller 300 controls the operation of the system. The controller 300 may receive feedback from one or more modules of the system and/or may provide control instructions to one or more modules of the system. The dashed lines in FIG. 1 between controller 300 and each of the modules indicate that the controller 300 may communicate with one or more of the modules of the system. In some embodiments, the modules of the system (e.g., the dispensers, the blender, the carriage, etc.) may also communicate with one another, with and/or independently of the controller.

Figure 2:
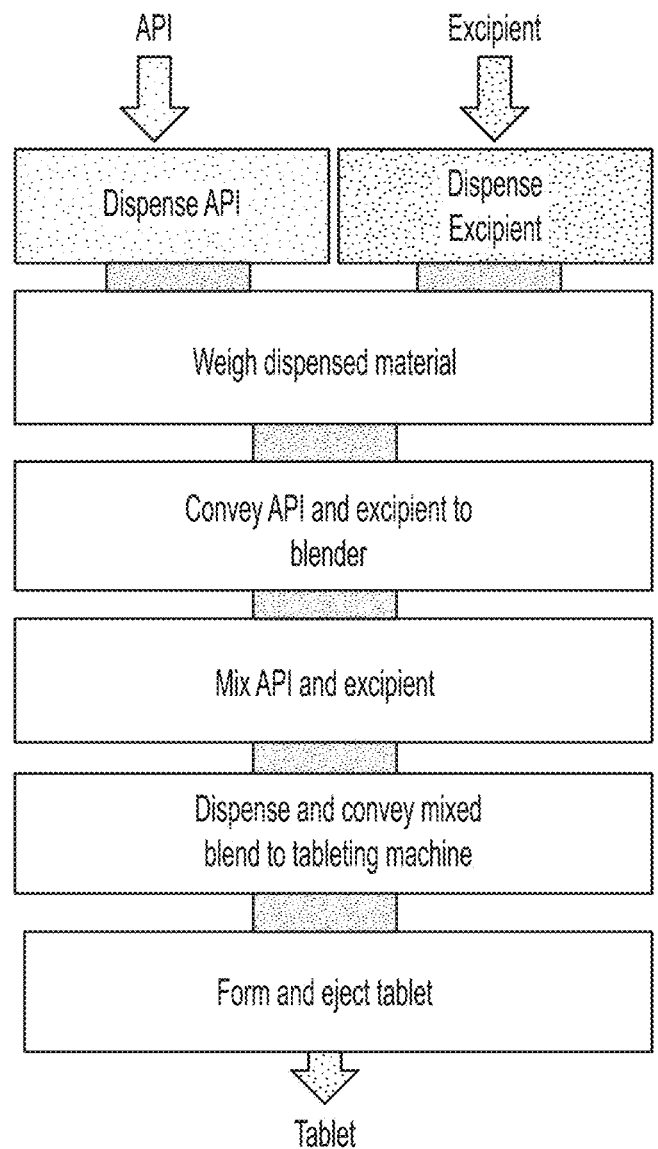
FIG. 2 is a block diagram of a method of producing pharmaceutical tablets according to one set of embodiments.

FIG. 2 depicts a schematic illustration of a process of producing pharmaceutical tablets according to one set of embodiments. In such embodiments, API and excipient are dispensed, then weighed. In some embodiments, the API and/or excipients may be solid, such as in a powder form. The API and excipient may be dispensed and weighed at different times, such that the system is able to determine the mass of each type of dispensed material. For example, the system may first dispense API and then weigh the dispensed API. The system may then subsequently dispense excipient and then weigh the dispensed excipient. In some embodiments the API may be dispensed into a carriage, and the excipient may be dispensed into the same carriage holding the dispensed API. The system may determine the mass of the excipient based on the increase in weight detected after the excipient was added. In other embodiments, each of the materials may be weighed separately. For example, the API and excipient may be weighed in different carriages. Or, the same carriage may be emptied out between receipt of each type of material. For example, in some embodiments, the API is first weighed, then the API is removed from the carriage. After the carriage is emptied, in some embodiments, the excipient is received and weighed in the carriage. For the above discussion, it should be appreciated that the order of dispensing can be changed, e.g., reversed such that the excipient is dispensed before the API. Or, in case where a plurality of excipients and/or APIs are used in a tablet, any order of dispense may be used.

In some embodiments, after weighing, the API and excipient are conveyed to a blender. In such embodiments, weighing occurs prior to conveying the API and excipient to the blender. However, in other embodiments, weighing may occur in the blender itself. In either case, with the API and excipient present in the blender, the blender mixes the API and excipient together into a mixed blend. In some embodiments, the mixed blend is then dispensed into smaller, discrete amounts that are received by a tableting machine, which forms and outputs a completed tablet. In some embodiments, the tableting machine may use a direct compression method to compact the mixed blend and form the tablet. In some embodiments, the final tablet may be weighed to check that it is of a desired mass.

Figure 3:
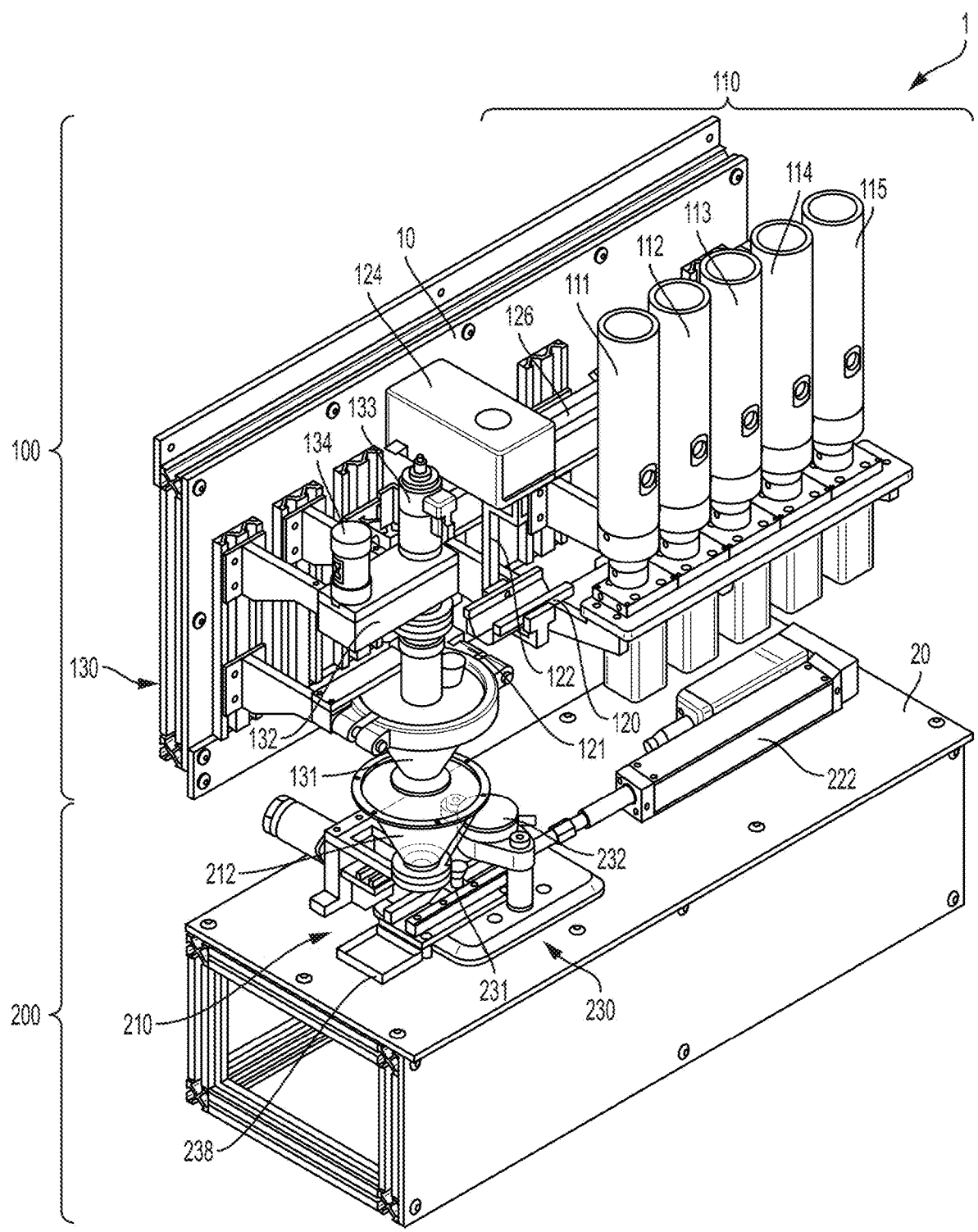
FIG. 3 is a perspective view of a system for producing pharmaceutical tablets according to one set of embodiments.
Figure 4:
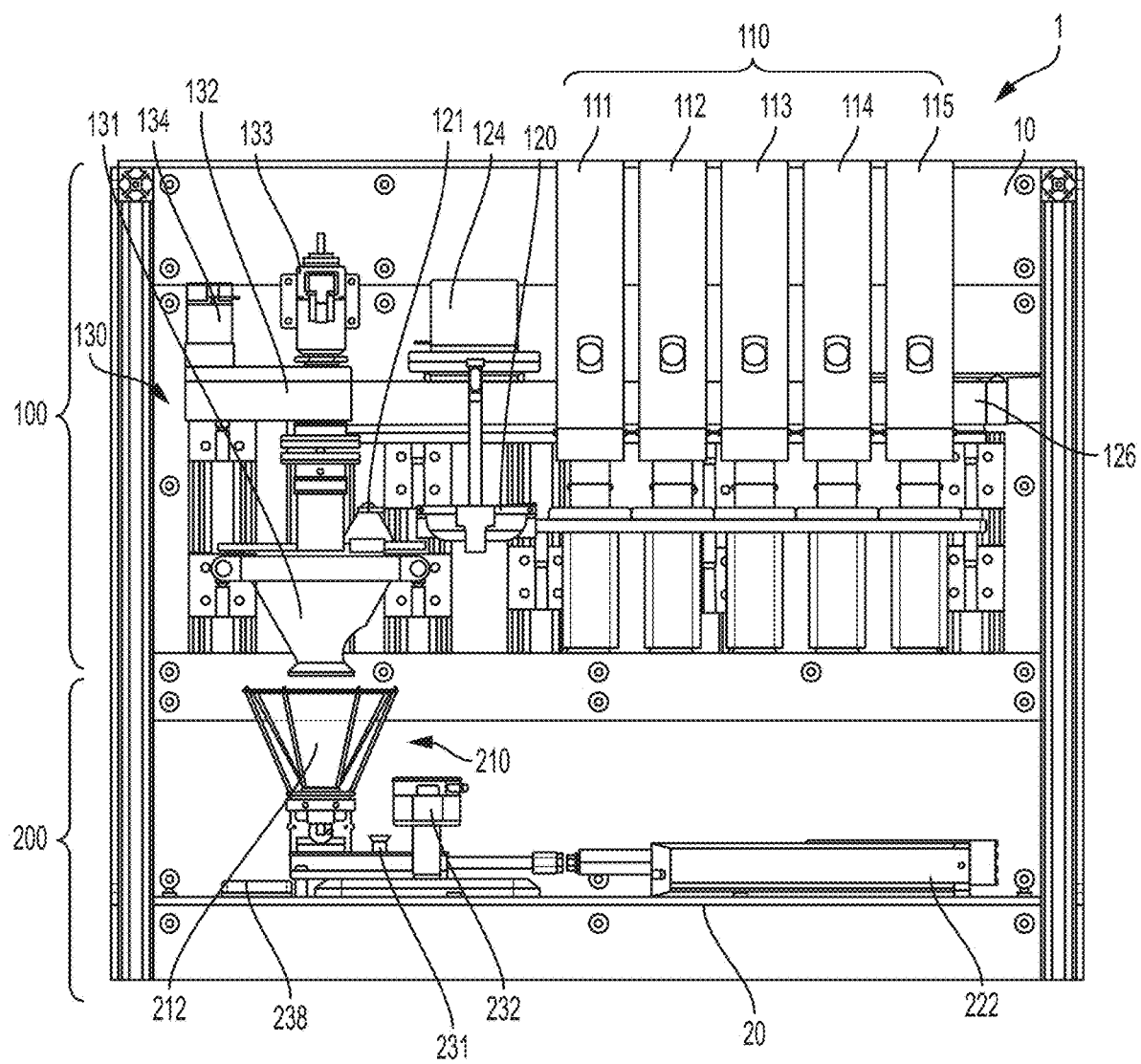
FIG. 4 is a front view of the system shown in FIG. 3.
Figure 5:
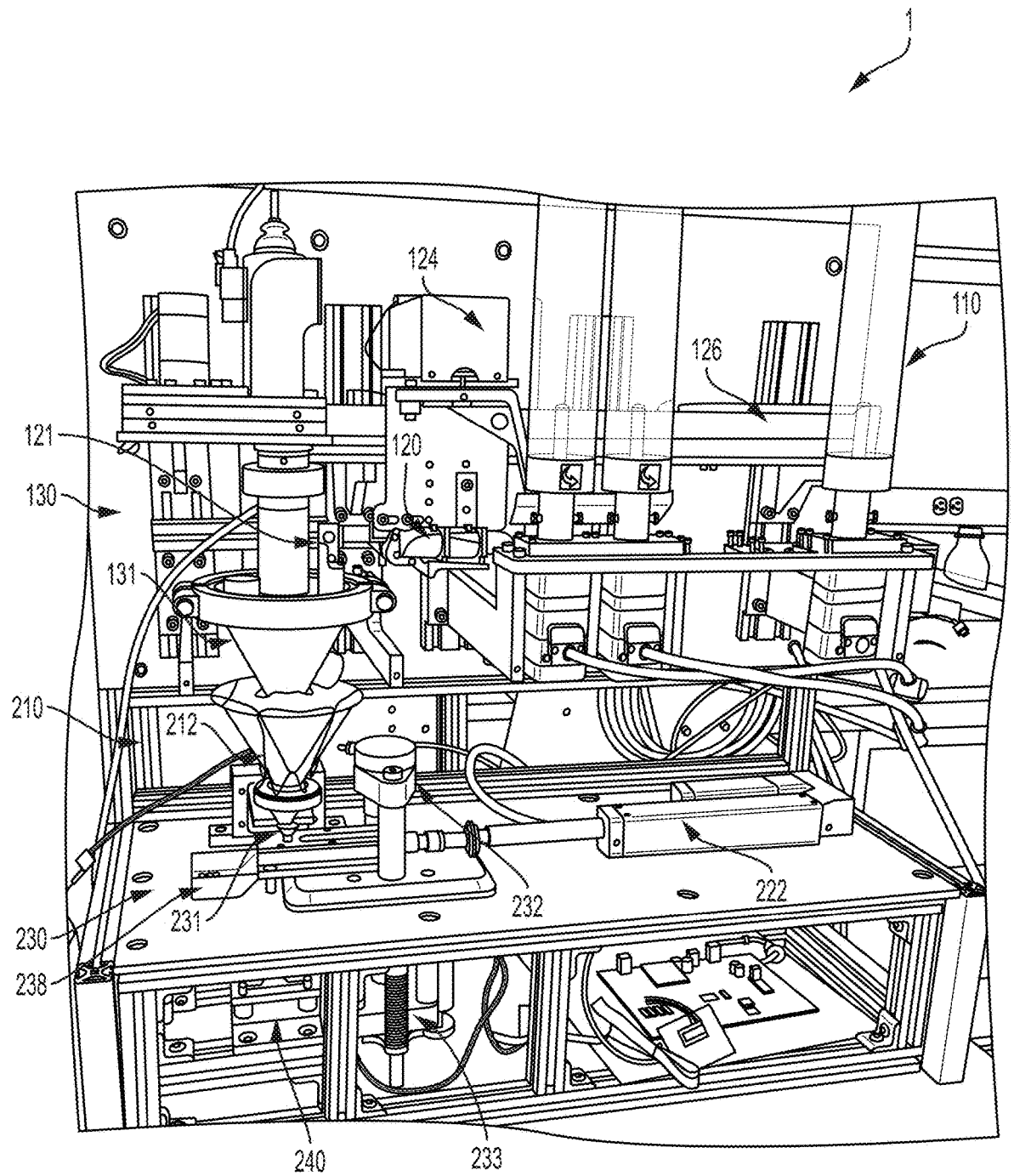
FIG. 5 depicts a system for producing pharmaceutical tablets.

One illustrative embodiment of a system for producing pharmaceutical tablets is shown in FIGS. 3 and 4, and an illustrative embodiment of one system is shown in FIG. 5. Each of the components mentioned in this section will be described in greater detail in a subsequent section. The tablet production system 1 includes a plurality of dispensers 110. In the embodiment of FIGS. 3 and 4, the system includes five dispensers, 111, 112, 113, 114 and 115. In this embodiment, the weigh module includes a weigh scale 124, a carriage 120 that receives material to be weighed, and an arm 122 connecting the weigh scale 124 to the carriage 120. In some embodiments, the weigh module also serves to convey dispensed material to the blender. For example, in the embodiment shown in FIGS. 3-5, the weigh scale is coupled to an actuator 126 such that the carriage 120 can be moved to various positions beneath each of the dispensers 110 and to the blender 130. In some embodiments, to facilitate delivery of material from the carriage 120 to the blender, the carriage is configured to tilt such that material in the carriage slides out into the blender. In some embodiments, the system may include a tilting mechanism 121 that tilts the carriage. In some embodiments, the blender 130 includes a rotating impeller that mixes the dispensed API and excipient together into a blended mix.

The blended mix is then transferred from the blender 130 to a dispenser 210. In some embodiments, the bottom of the blender 130 opens up and feeds into the dispenser 210 located below. In some embodiments, the blended mix dispenser 210 dispenses discrete amounts of the blended mix into a tableting unit 230, which compresses the blended mix into a tablet and ejects the tablet into a tablet output tray 238.

According to one aspect, the system may be divided into two process streams: an upper process stream 100 and a lower process stream 200. In the embodiment shown in FIGS. 3-5, the upper process stream 100 begins with the dispensers 110 and ends with the blender 130 mixing the API and excipient into a blended mix. The lower process stream 200 begins with the blended mix dispenser 210 receiving a blended mix and ends with the tableting unit 230 forming and outputting a tablet. The step of transferring the blended mix from the blender 130 to the blended mix dispenser 210 connects the upper and lower process streams. In the embodiment shown in FIGS. 3-5, this transfer step occurs via an opening of the blender 130 to allow blended mix inside the blender 130 to fall into the dispenser 210 below. In some embodiments, the upper and lower process streams can operate simultaneously, and, in some cases, independently of one another. For example, while API and excipient are being dispensed, weighed, and mixed in the blender in the upper process stream, tablets can be formed in the lower process stream. The two process streams may be controlled by either the same controller or separate controllers.

In the embodiment shown in FIGS. 3-5, the upper and lower process streams occur at the same physical location. In addition, with the blender directly ejecting blended mix into the dispenser 210 below, the two process streams also interact directly with one another.

However, it should be appreciated that the upper and lower process streams may be physically separated from one another. For example, the two process streams may occur in separate facilities in different parts of the world. The upper process stream may result in a mixed blend that is transported to the location of the lower process stream, and the mixed blend is fed into the dispenser of the lower process stream. The two process streams may also occur in the same facility, but in separated positions such that the blender of the upper process stream is not directly above the dispenser of the lower process stream.

In some embodiments, the upper and lower process streams need not be tied together. For example, in some embodiments, the upper process stream can supply an unrelated tableting stream. As another example, in some embodiments, the lower process stream can be supplied by an unrelated blending stream.

According to one aspect, each of the upper and lower stream processes are integrated systems. In contrast to conventional large-scale batch processes, in which the components are spread out over the floor of the facility due to their large-volume nature, for each of the upper and lower stream processes, in some embodiments, the components are sized and positioned such that they can be coupled to a common frame, making the system compact, and in some cases, portable. For example, in the embodiment shown in FIG. 3, the components of the upper process stream 100, e.g., the dispensers 110, weigh scale 124, carriage 120 and blender 130 are coupled to an upper frame 10. As also seen in FIG. 3, the components of the lower process stream 200, e.g., the dispenser 210 and the tableting unit 230, are coupled to a lower frame 20.

According to one aspect, the tablet production system is a compact, portable unit. In some embodiments, the tablet production system occupies a volume of less than 10,000 liters, less than 5000 liters, less than 2000 liters, or less than 1000 liters. As used herein, the "volume" of the system corresponds to the smallest rectangular prism that encompasses all components of the system. In some embodiments, the tablet production system has a footprint of less than 10 square meters, less than 5 square meters, less than 2 square meters, or less than 1 square meter. In one embodiment, the tablet production system is approximately 72.4 cm×53.3 cm×134.6 cm (length by width by height).

Figure 6:
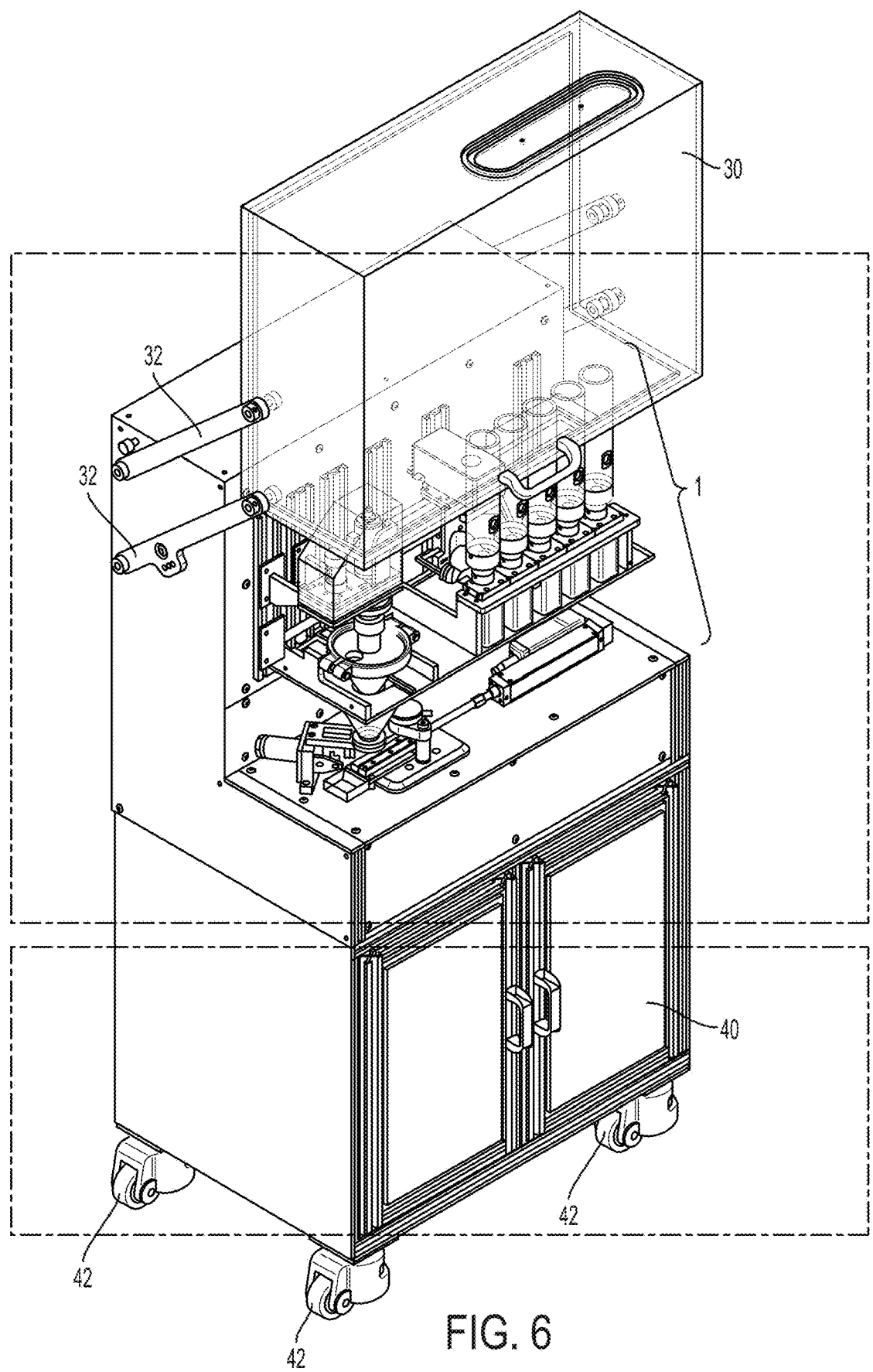
FIG. 6 is a perspective view of a system for producing pharmaceutical tablets in a portable arrangement according to one set of embodiments.

According to one aspect, the tablet production system can be one complete integrated system, with both the upper and lower process streams contained within one compact, portable unit. In some embodiments, the tablet production system can sit atop a rolling assembly, such that the system can be easily moved and transported. In one illustrative embodiment shown in FIG. 6, the tablet production system 1 is integrated with a rolling assembly having wheels 42. The rolling assembly may include locks on the wheels that can be engaged to prevent inadvertent movement of the system and disengaged to permit movement of the system.

In some embodiments, the assembly may include a removable access covering that can be moved to provide access to the production system. In the illustrative embodiment shown in FIG. 6, the assembly includes a covering 30. The covering 30 may be mounted to the sides of the system via arms 32 that can rotate up and down to permit the covering 30 to move between closed and open positions. In the open position, a user is able to access the components of the system 1 and can proceed with any appropriate manipulations of the system, e.g., for maintenance, cleaning, changing of components, etc. In some embodiments, the covering 30 may be transparent in order to allow a user to see the tablet production system while the covering 30 is in the closed position. In some embodiments, a storage/equipment cabinet 40 may be provided with the production system 1.

In some embodiments, the system may be configured to manufacture on-demand pharmaceutical tablets on a scale of one hundred to thousands a day. Examples of different types of drugs that may be manufactured by such a unit include, but are not limited to: ibuprofen, doxycycline monohydrate, diphenhydramine hydrochloride, diazepam, ciprofloxacin HCl, azithromycin and fluoxetine hydrochloride. In some embodiments, the same system may be configured to produce two or more different drugs, even if the drugs are from different drug classes and have differing chemical structures, bulk physical properties, flow behaviors, and/or require different formulation strategies to make tablets. According to one aspect, the tablet production system is designed to accommodate a wide range of materials and tablet formulations.

Each of the components of the tablet production system will now be discussed in more detail below.

Figure 7:
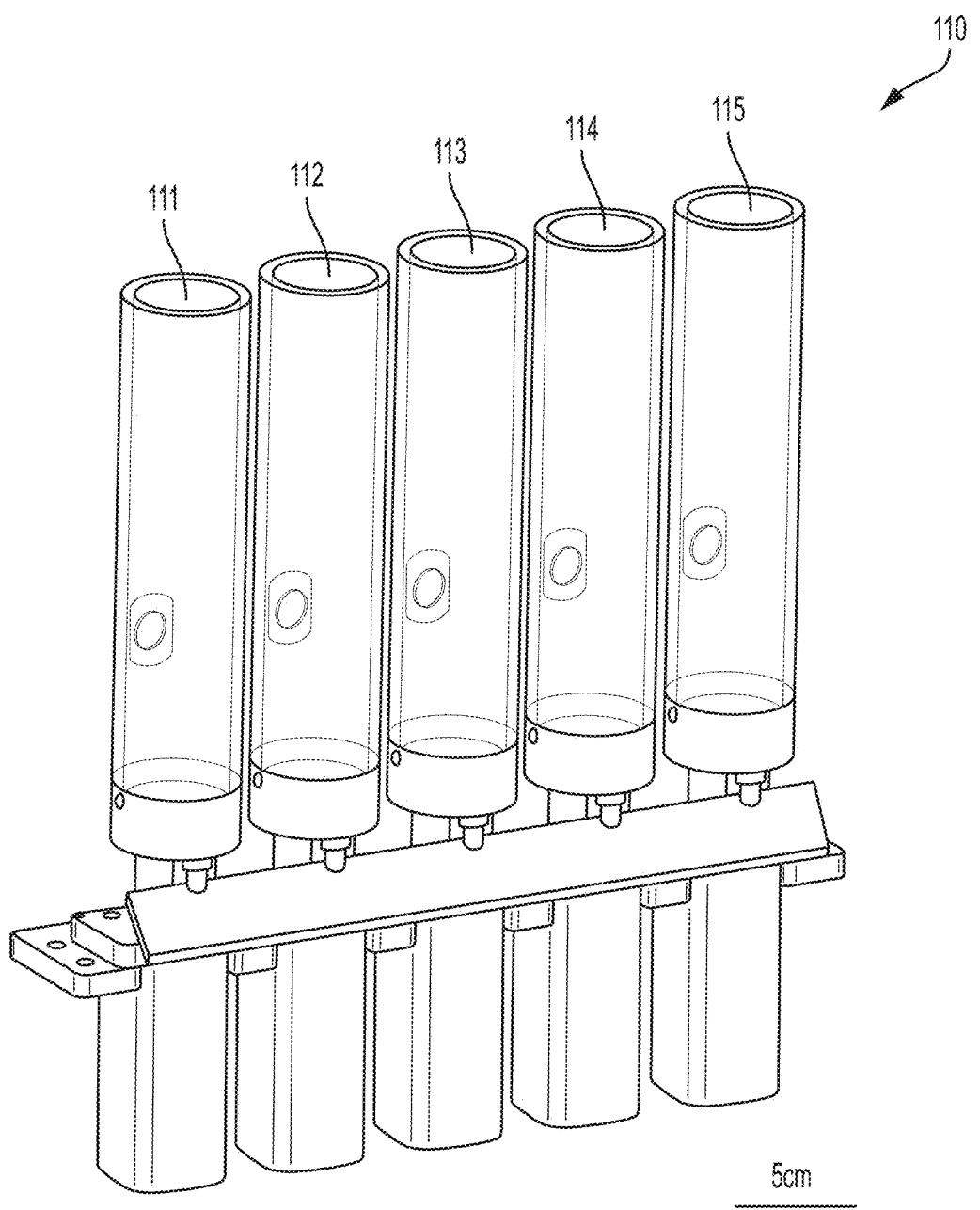
FIG. 7 is a perspective view of an array of dispensers according to one set of embodiments.
Figure 8A:
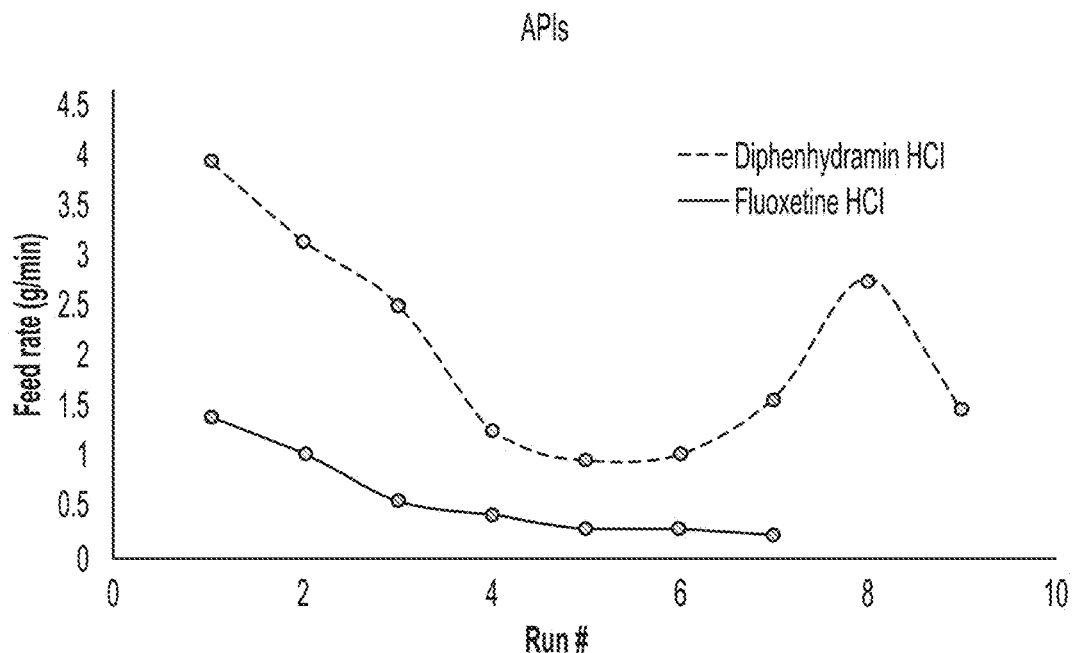
FIGS. 8A-8D depict graphs indicating dispenser performance.
Figure 8B:
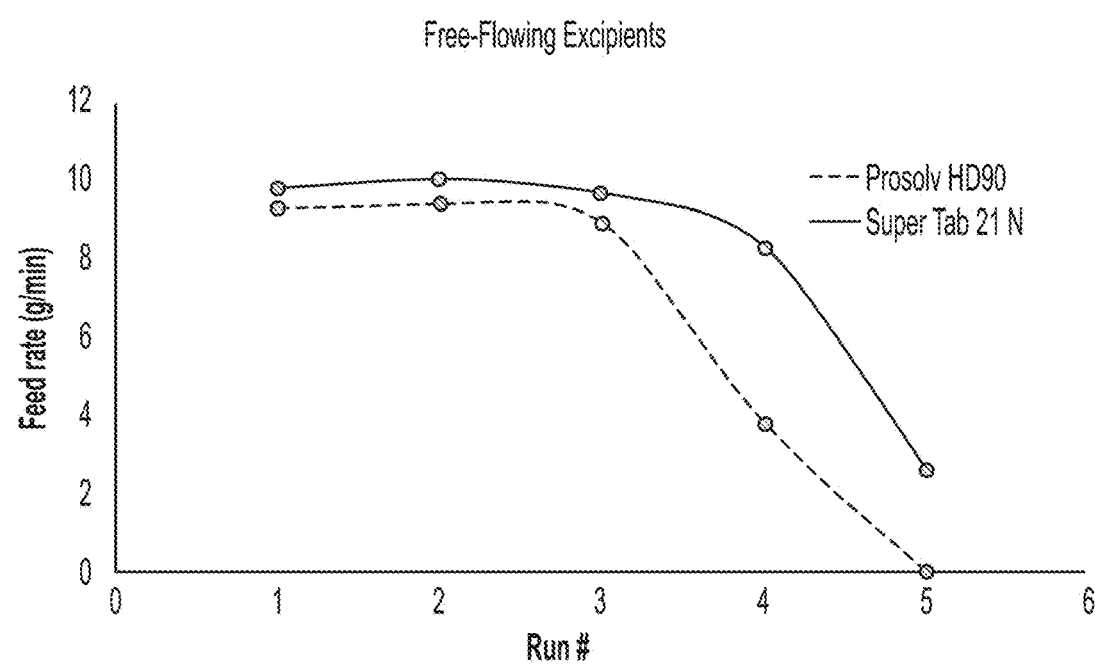
Figure 8C:
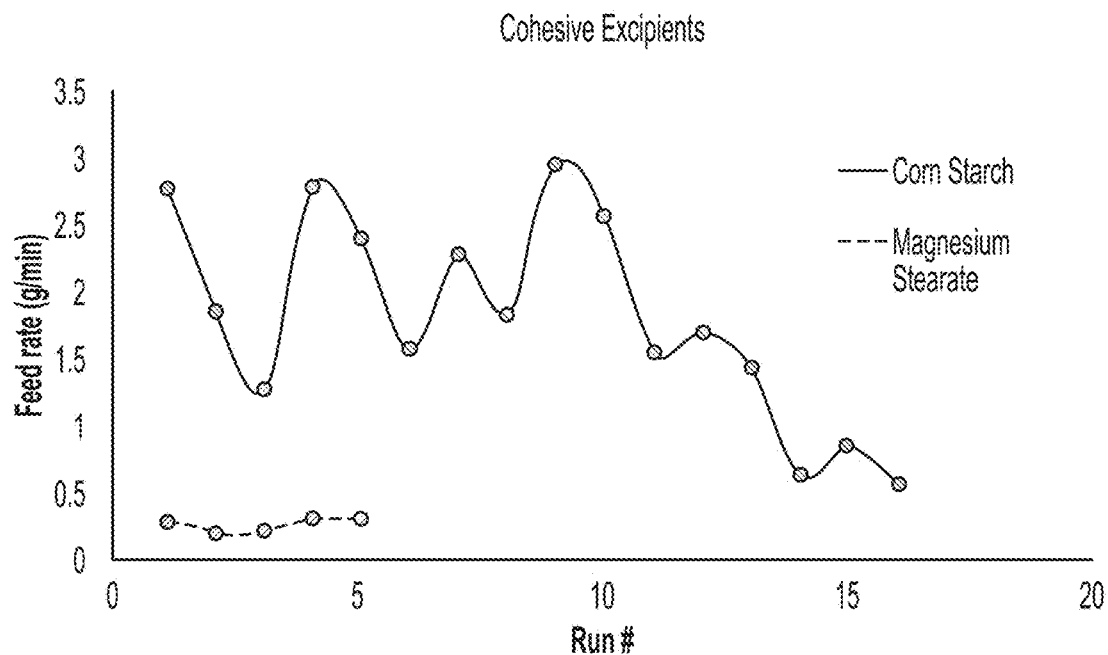
Figure 8D:
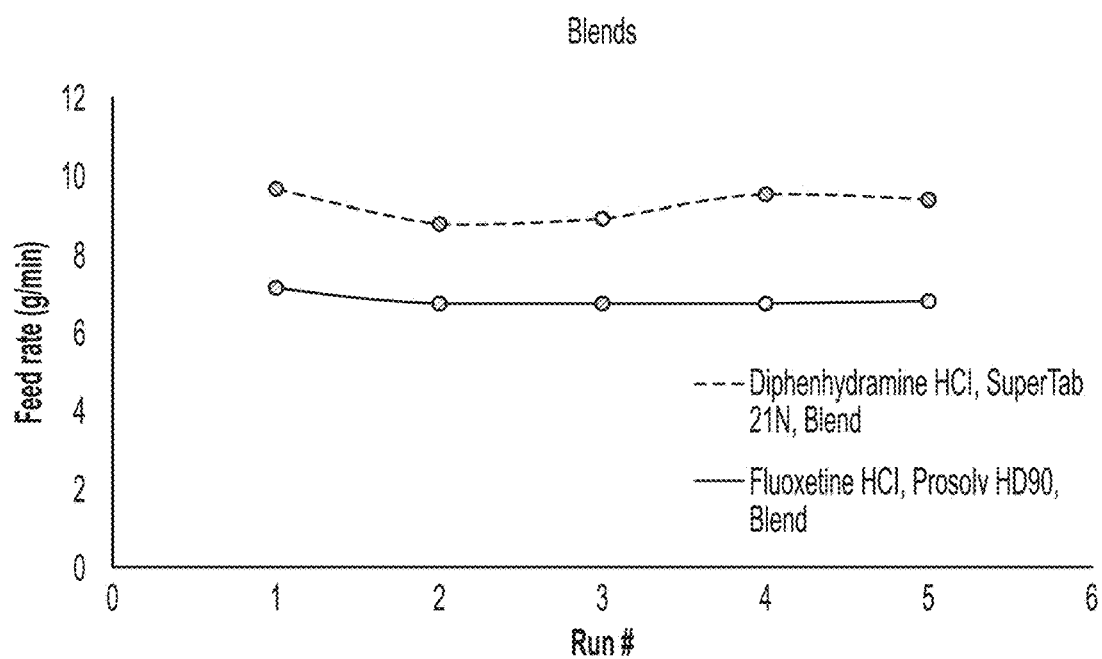

One illustrative embodiment of dispensers that may be used with the tablet production system is shown in FIG. 7. A plurality of dispensers may be used—each containing a different material. In some embodiments, the dispensers contain API, excipients or other suitable tablet ingredients. Although five dispensers are used in the FIG. 7 embodiment, it should be appreciated that any suitable number of dispensers may be used. For example, 2, 3, 4, 5, 6 or more dispensers may be used.

In some embodiments, the dispensers are volumetric feeders in which feed rate is inferred from feeder speed based on prior calibration. In other embodiments, the dispensers are gravimetric feeders in which feed rate is controlled based on direct weight measurement.

Figure 25:
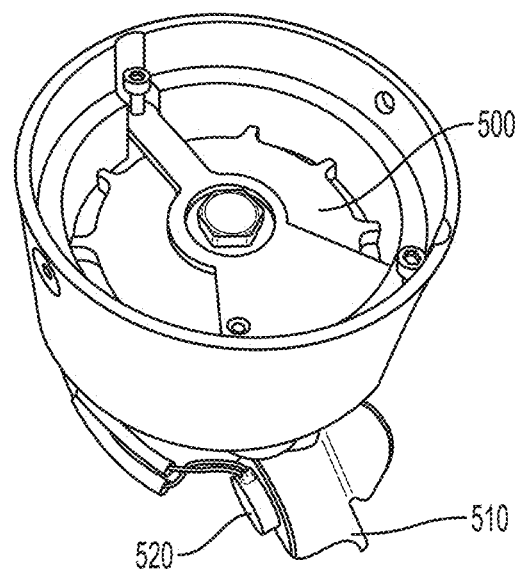
FIG. 25 depicts a dispenser with a discharge chute and a vibratory mechanism.

In the embodiment shown in FIG. 7, the dispensers are Orbetron 50 Series dispensers (ORBETRON, Hudson, Wis.). Such dispensers operate by rotating a feeding disc within a storage container. An illustrative disc 500 is shown in FIG. 25. In some embodiments, the feeding disc has a small hole into which material can fall. With each rotation of the feeding disc, the material that is positioned in the hole of the feeding disc becomes aligned with an outlet hole of the dispenser, allowing the material in the disc hole to exit the dispenser. In this manner, with each rotation, the feeding disc permits a limited amount of material to exit the dispenser. In some embodiments, a "flicker" component may be added to a dispenser to aid in dispensing of cohesive materials. Such a component may help to break powder bridges and enhance flow.

The inventors have appreciated other arrangements to help with decreasing compaction of powder and/or otherwise preventing clogging of dispensers.

Figure 26:
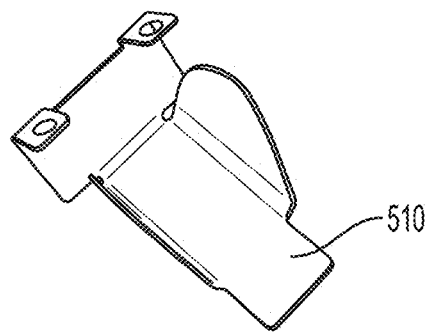
FIG. 26 depicts a dispenser discharge chute.

In some embodiments, as shown in FIGS. 25-26, the dispenser may include a chute 510 downstream of the outlet of the dispenser. The chute may be attached directly to the dispenser outlet. The chute may aid in dispensing material out of the dispenser.

Figure 27:
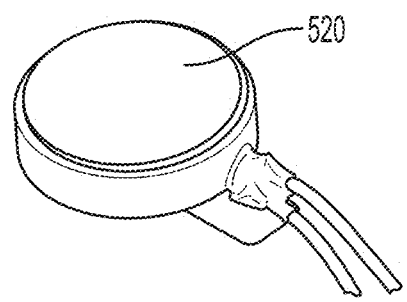
FIG. 27 depicts a vibratory mechanism.

In some embodiments, as shown in FIGS. 25 and 27, a vibratory mechanism 520 may be added to the dispenser. The vibratory mechanism may help to prevent compaction of material being dispensed and/or help to prevent clogging of the dispenser outlet. The vibratory mechanism may help to reduce powder accumulation on one or more components of the dispenser. The vibratory mechanism may be positioned directly on the dispenser outlet itself, or on a component attached to the dispenser outlet, such as the chute 510. One example of a vibratory mechanism is an ADAFRUIT vibrating mini motor disc. In some embodiments, the operating voltage of the vibrating mini motor disc is 2 to 5 volts.

Figure 28:
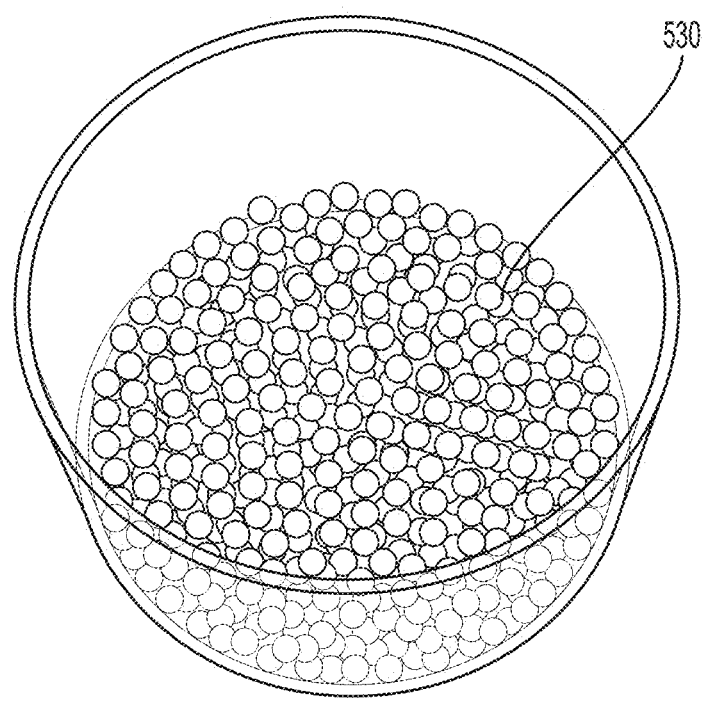
FIG. 28 depicts a plurality of glass beads to help with dispensing of material.

In some embodiments, beads may be added inside the dispenser to help decrease compaction of powder. The beads may be sized such to remain inside the dispenser without jamming the dispenser. For example, the beads may be larger than the dispenser outlet. In some embodiments, in dispensers that utilize a rotation disc, the beads may be sized larger than the spaces between the teeth of the disc such that they do not fall into the spaces between the teeth of the disc. The beads may move as the disc rotates, which may help to break any compacted material and keep the powder flow continuous. An illustrative example of such beads is shown in FIG. 28, which depict a plurality of glass beads. In some embodiments, the beads may be 5 mm in diameter. However, other diameter sizes may be used as well. In some embodiments, 10 to 30 grams of the glass beads may be used. In some embodiments, about 18 grams of the glass beads may be used.

In some embodiments, the dispensers may operate at a feed as low as 2 gm/hour and as high as 5 kg/hour. The flow rate of the dispensers may be sufficient for a thousand doses a day.

It should be appreciated that other types of dispensers may be used, such as screw feeders, vibrator feeders, roller feeders, belt feeders, etc.

FIGS. 8A-8D depict graphs indicating performance of the Orbetron 50 Series dispensers using an open-loop arrangement (i.e., no feedback from a weigh scale was used to control the dispensers). Tests were conducted with API, free-flowing excipients, cohesive excipients, and blends. The outcome of the tests indicated that higher variations in feed rate were observed for API and cohesive excipients, lower variations in feed rate were observed with free-flowing excipients and blends, and that feed rate varied with the change of fill level or powder height.

In some embodiments, to resolve these types of variations, a closed-loop control of dispensed powder may be included in the tablet production system. As one example, a weigh scale may be used to provide closed-loop feedback control. The weigh scale arrangement will be discussed in more detail in the next section.

In some embodiments, the tablet production system may include a weigh scale to provide a closed-loop control of dispensed powder. In some embodiments, the weigh scale takes the form of a load cell. It should be appreciated that other types of weigh scales may be used, such as a piezoresistive sensor, force restoration balances, etc.

In some embodiments, API and excipients are fed from multiple dispensers to a carriage suspended from a load cell. In some embodiments, the API and excipients from the plurality of dispensers are dispensed directly into a blender. In such an arrangement, the entire blender itself may be suspended from a load cell or other weigh scale such that material being dispensed into the blender may be weighed.

In some embodiments, material dispensed from the dispensers must be conveyed to a blender. In some embodiments, the component of the tablet production system that performs a weighing function of dispensed material also performs an additional function of conveying dispensed material to the blender for mixing.

Figure 9:
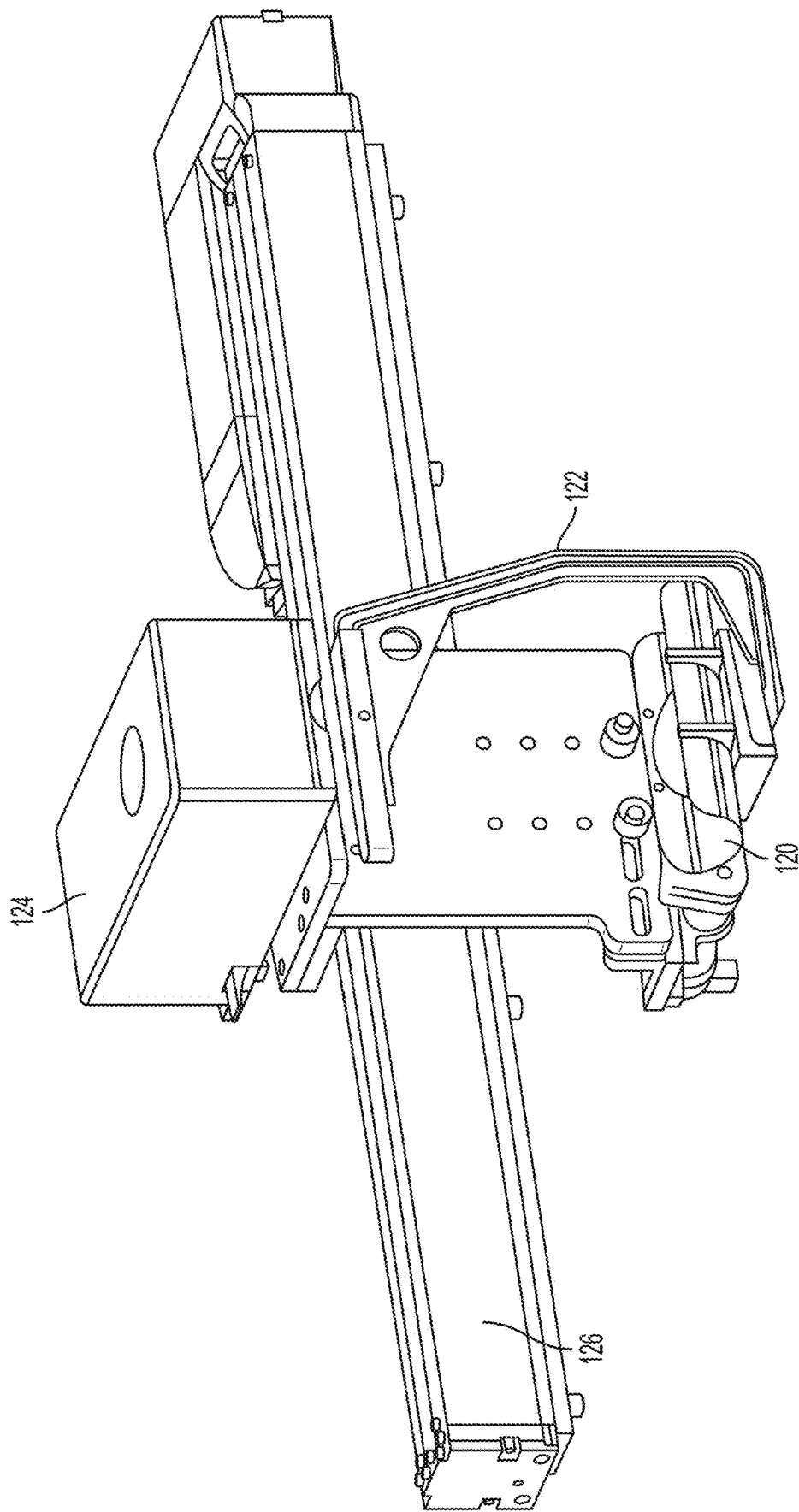
FIG. 9 is a perspective view of a material carrying unit according to one set of embodiments.
Figure 10:
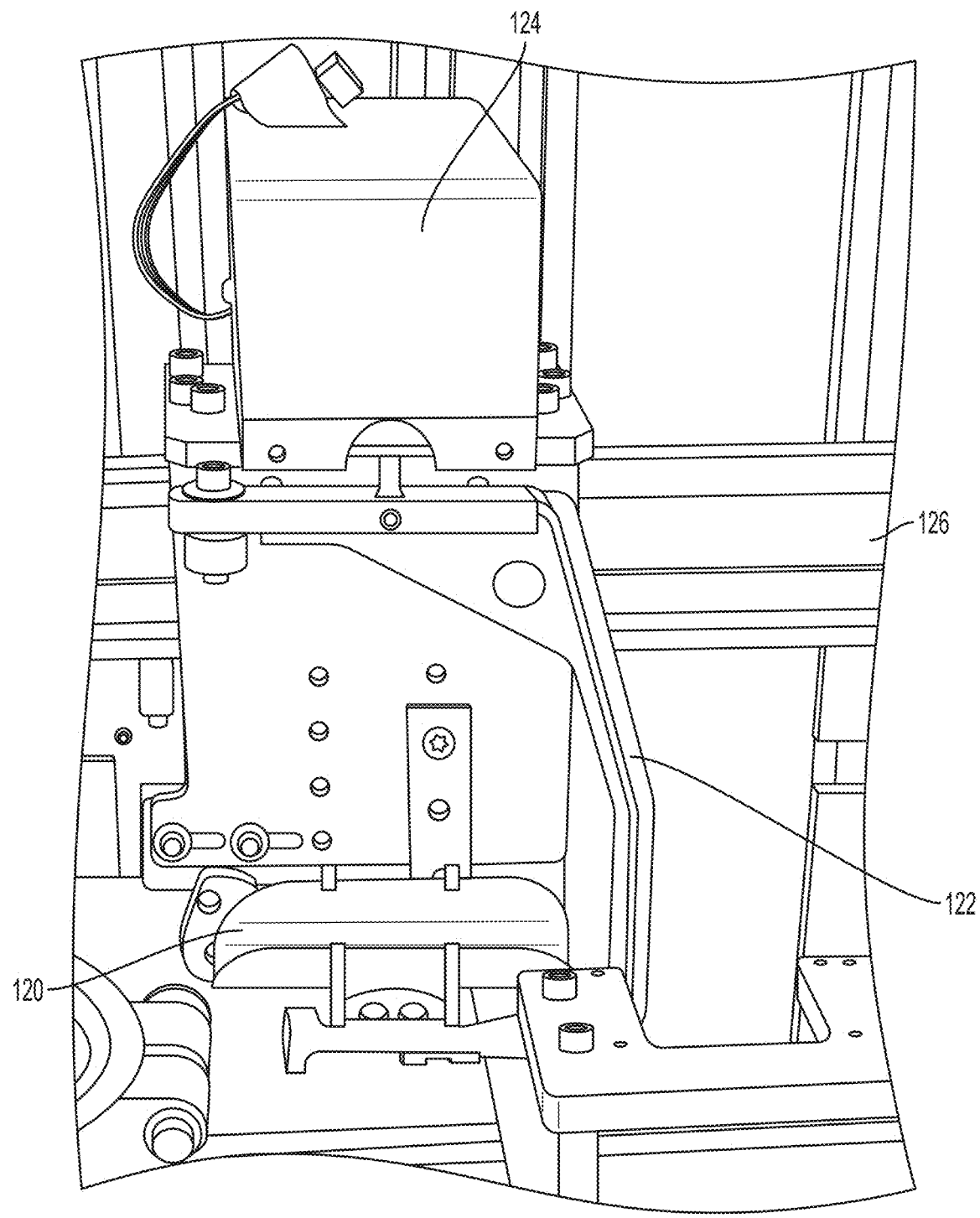
FIG. 10 depicts a material carrying unit.

One illustrative embodiment of a weigh scale module is shown in FIG. 9, and an actual weigh scale module is shown in FIG. 10. The module of FIGS. 9-10 includes a weigh scale 124 and a carriage 120 suspended from the weigh scale 124 via an arm 122. In the embodiment shown in FIGS. 9 and 10, the weigh scale 124 comprises a load cell. In some embodiments, the weigh scale module also performs an additional function of conveying material. In some embodiments, the module may include a linear actuator 126 to move the weigh scale 124, arm 122 and carriage 120 to different locations. In some embodiments, the carriage 120 can be commanded to move to any dispenser, in any sequence, and the required amounts of powder or other material may be dispensed at each dispenser location. The carriage 120 may then transfer material to a blender. In some embodiments, the module may include a track along which the components can slide.

The inventors have appreciated that one potential challenge in transferring material from one container to another, particularly where the material is a powder, is the tendency for some of the material to remain in the starting container, resulting in incomplete transfer of material. This may lead to improper ingredient ratios and/or waste.

In some embodiments, where an intermediate carriage is used to carry material from dispensers to a blender, the carriage is arranged to tilt to aid in transfer of material. In some embodiments, such as the embodiments of FIGS. 9 and 10, the carriage 120 may be pivotally attached to the arm.

In some embodiments, the system may include a tilting mechanism, which could be, for example, on the blender, in a stationary position above the blender, or on the carriage itself. When the carriage reaches the blender, the tilting mechanism may be actuated to tilt the carriage. In the embodiment shown in FIGS. 3-5, the system includes a powered tilting mechanism in the form of a forklift 121 positioned above the blender 130. When the carriage 120 reaches the blender, the forklift 121 lifts the trailing end of the carriage to tilt the leading edge of the carriage downward toward the mixing vessel of the blender.

In other embodiments, the tilting of the carriage may be done in a passive manner instead of by a powered tilting arrangement. For example, as the carriage moves toward the blender, the carriage may interact with a physical obstruction, such as a sloped wedge, that pushes one end of the carriage upward to tilt the carriage.

According to another aspect, material may be dispensed from the dispensers into the carriage in a particular order to facilitate transfer of material out of the carriage. In some embodiments, a controller controls the system to specifically dispense the least cohesive material into the carriage first. Without wishing to be bound by theory, when in contact with the originating container, cohesive materials tend to leave more residue than less cohesive materials during transfer. Thus, having the least cohesive material in direct contact with the carriage may help to facilitate a cleaner transfer.

Tests were conducted of the amount of residue remaining in the material carrying carriage when used to transfer a powder material. As seen in the test results depicted in FIG. 11, around 1% of the starting powder remained stuck to the carriage after transfer.

According to one aspect, the tablet ingredients are mixed until a desired amount of blend uniformity is reached. In some embodiments, the mixing can be performed by a blender.

Figure 12:
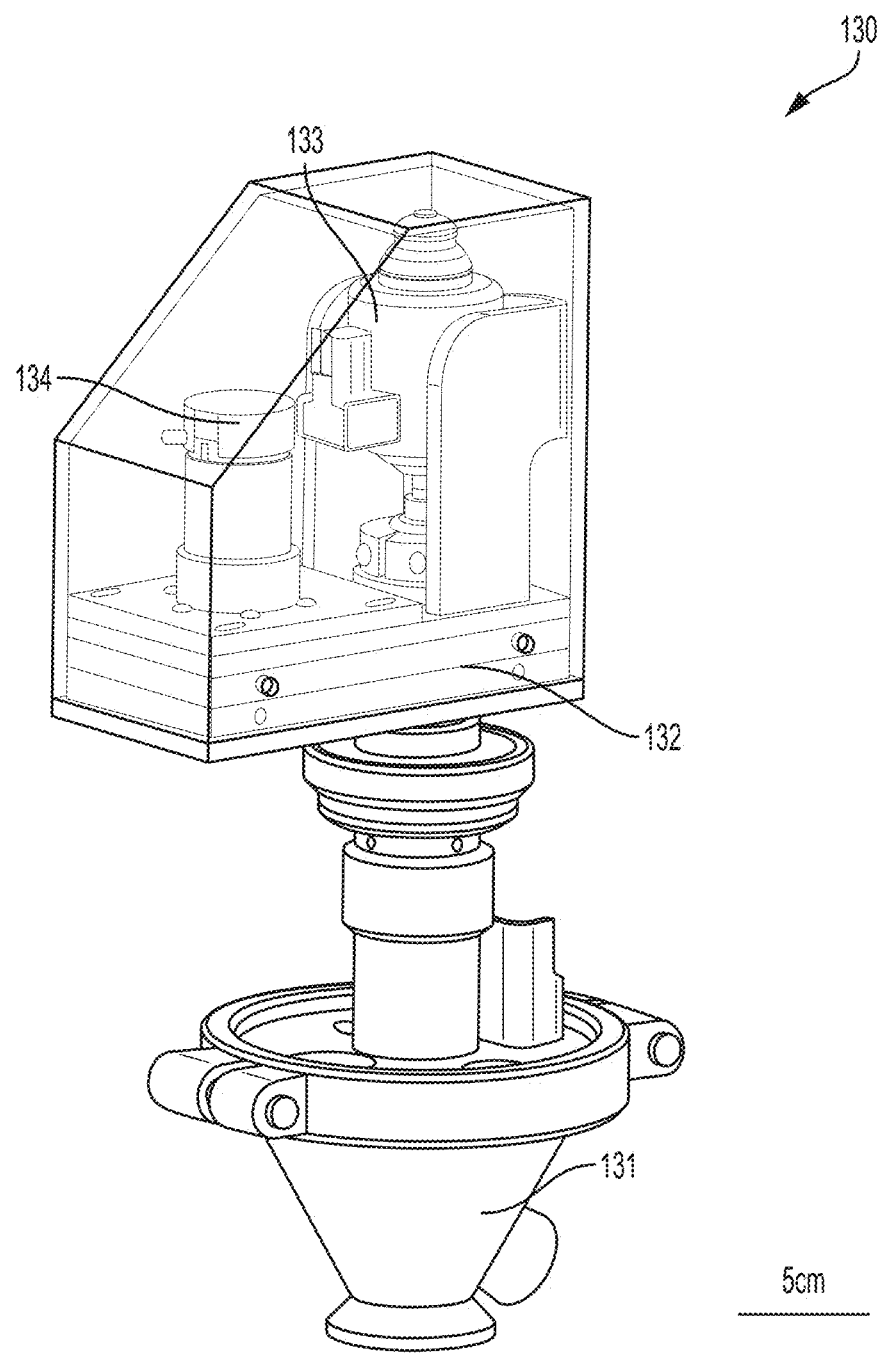
FIG. 12 is a perspective view of a blender according to one set of embodiments.
Figure 13:
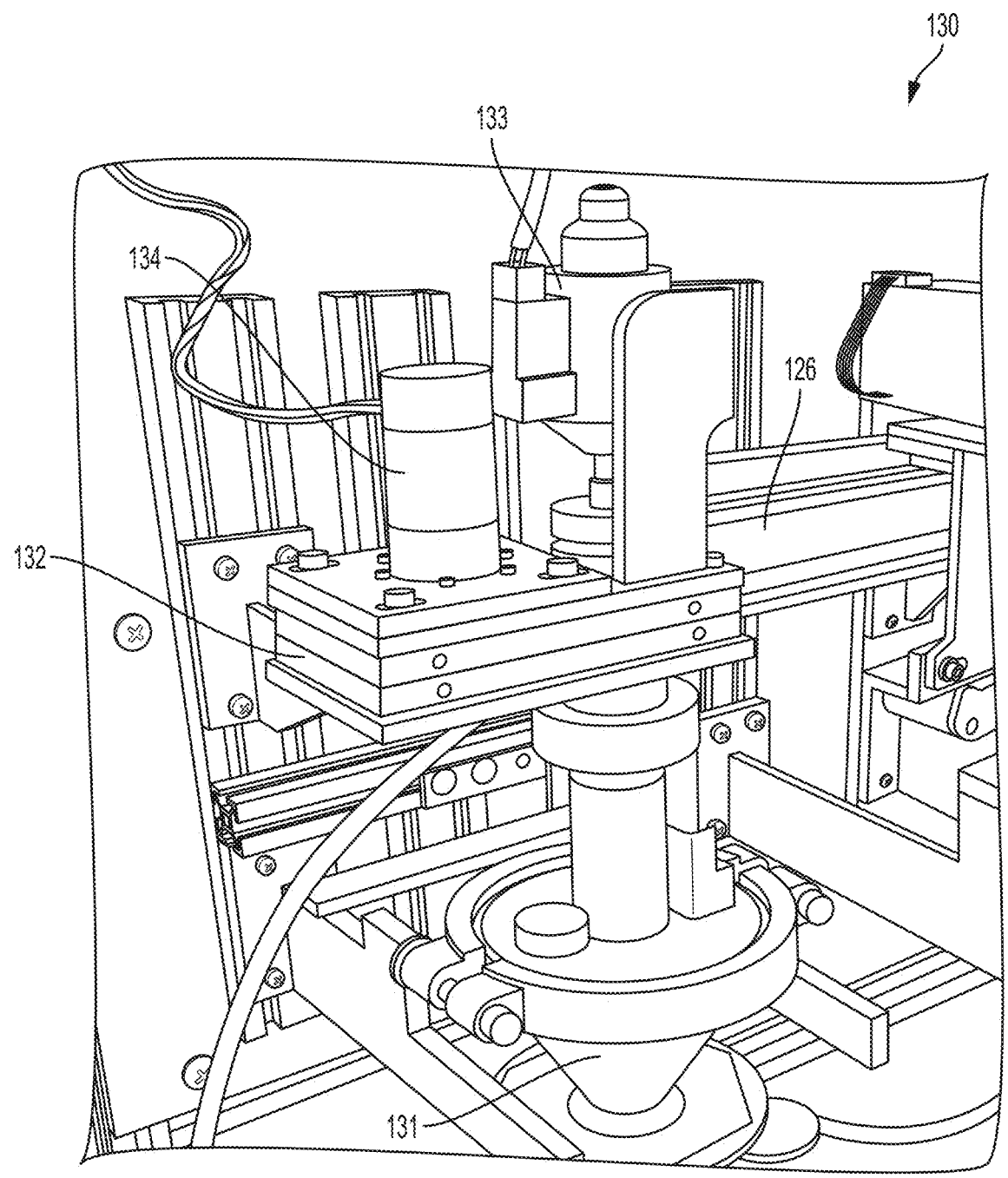
FIG. 13 depicts a blender.

One illustrative embodiment of a blender is shown in FIGS. 3, 4, 5, 12 and 13. As best seen in FIGS. 12-13, the blender 130 may include a mixing vessel 131, motor 134, an actuator 133, and a gearbox 132.

According to one aspect, the mixing vessel of the blender may be sized to be much smaller than the mixers used in traditional large-scale batch processing. In some embodiments, the mixing vessel of the blender may have a volume of less than or equal to 10 L, 1 L, 500 mL, 200 mL, or 100 mL. In some embodiments, the mixing vessel of the blender has a volume of about 200 mL. In some cases, the blender can mix about 50 gm of powder at a time with 40-50% capacity.

In some embodiments, the materials dispensed from the dispensers 110 form a mixture in the blender having a combined volume of less than or equal to 10 L, 1 L, 500 mL, 200 mL, or 100 mL.

According to one aspect, the blender is configured to be easily cleanable and re-configurable. In some embodiments, the blender includes a magnetic drive coupling, quick detach mount, and enclosed drive.

Figure 14A:
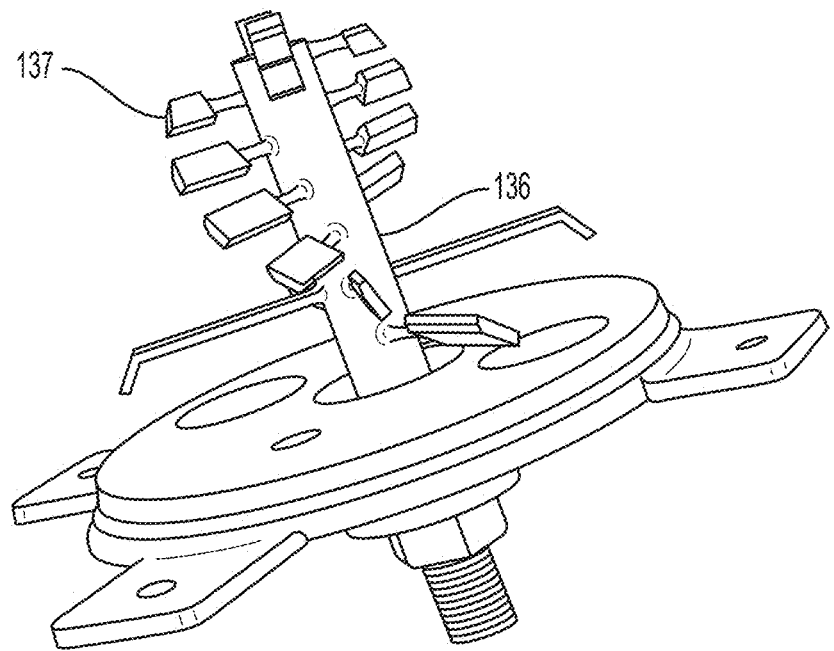
FIGS. 14A-14B depict a blender impeller.
Figure 14B:
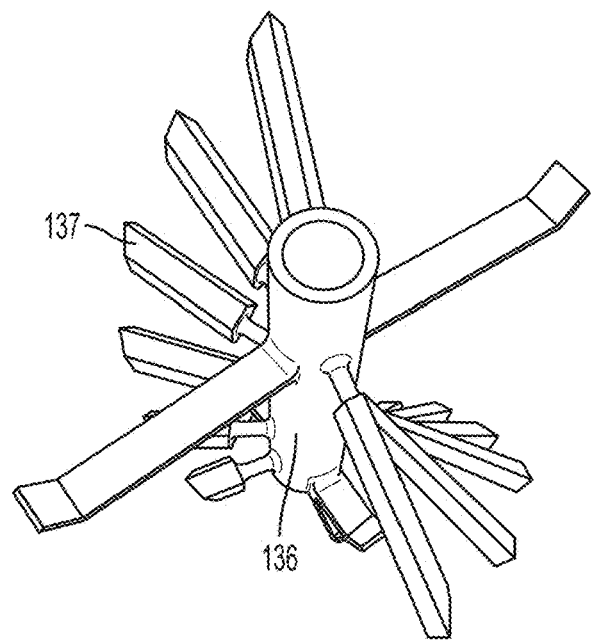
Figure 14C:
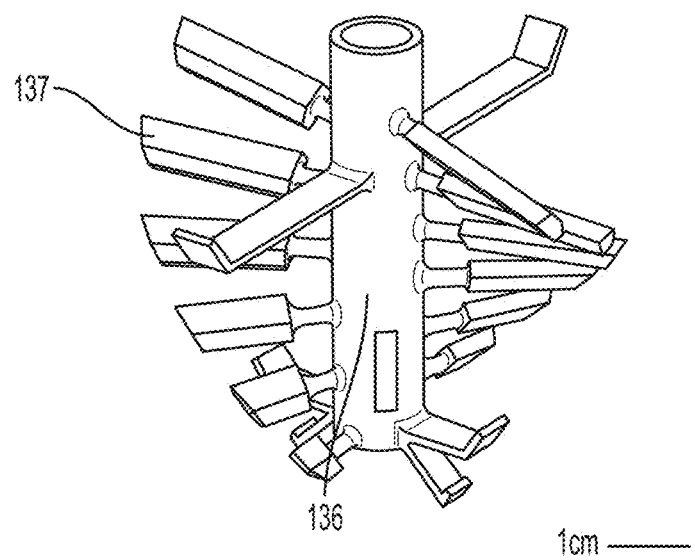
FIG. 14C is a perspective view of a blender impeller.

One illustrative embodiment of a blender impeller is shown in FIGS. 14A-C. The impeller includes a shaft 136 and a plurality of impeller blades 137. The blades 137 may be arranged at rotated angles relative to one another. Alternatively or in addition, for each group of blades (one on each side of the shaft), the blades 137 may be positioned at different heights relative to one another and/or at different circumferential positions along the drive shaft relative to one another. In some embodiments, the impeller may give rise to convective mixing to achieve a uniform blend.

In some embodiments, the blender may include a mechanism that allows for release of contents through the bottom of the blender mixing vessel to facilitate transfer of mixed material out of the blender.

In some embodiments, the blender mixing vessel has an outlet valve, such as a bottom plug, that can be opened to permit release of material. In one embodiment, a solenoid actuator pushes down on a shaft that is co-axial with the blender impeller shaft to move the bottom plug downwards so the mixed blend can be transferred to a dispenser below.

Figure 15:
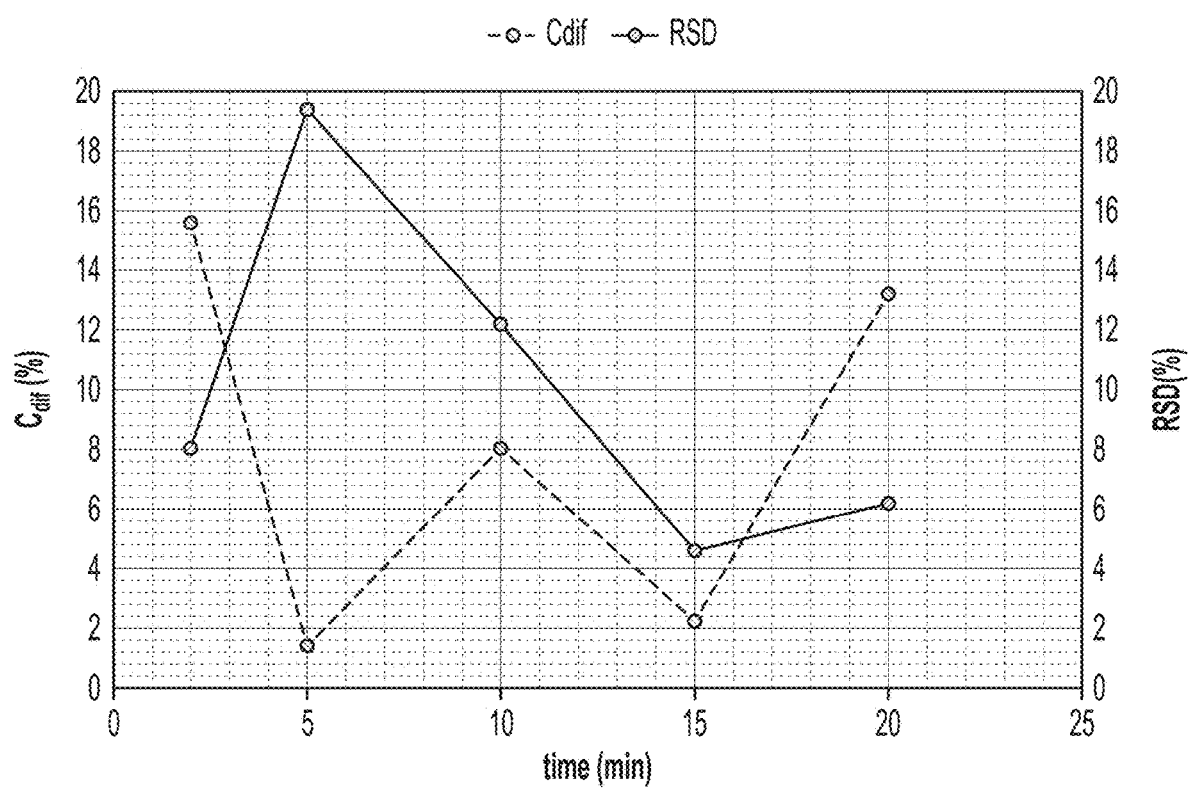
FIG. 15 depicts a chart indicating blender mixing performance.

Mixing performance of the blender was tested using 4.48% fluoxetine HCl+0.5% SiO2+95.02% corn starch. As seen in the test results depicted in FIG. 15, after about 15 minutes of mixing, the RSD (Relative Standard Deviation) reached <6%.

Figure 16:
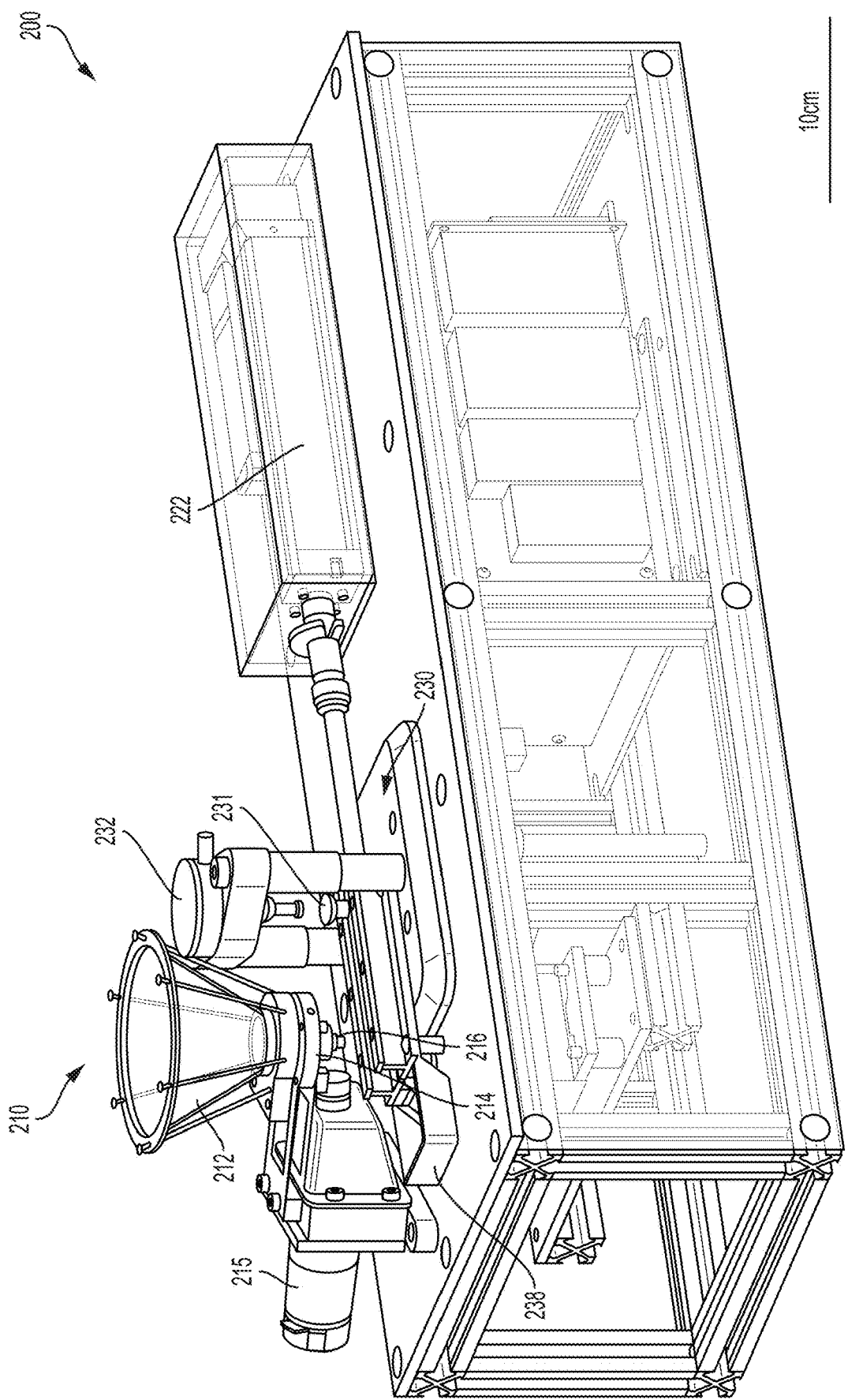
FIG. 16 is a perspective view of a lower stream process arrangement according to one set of embodiments.
Figure 17:
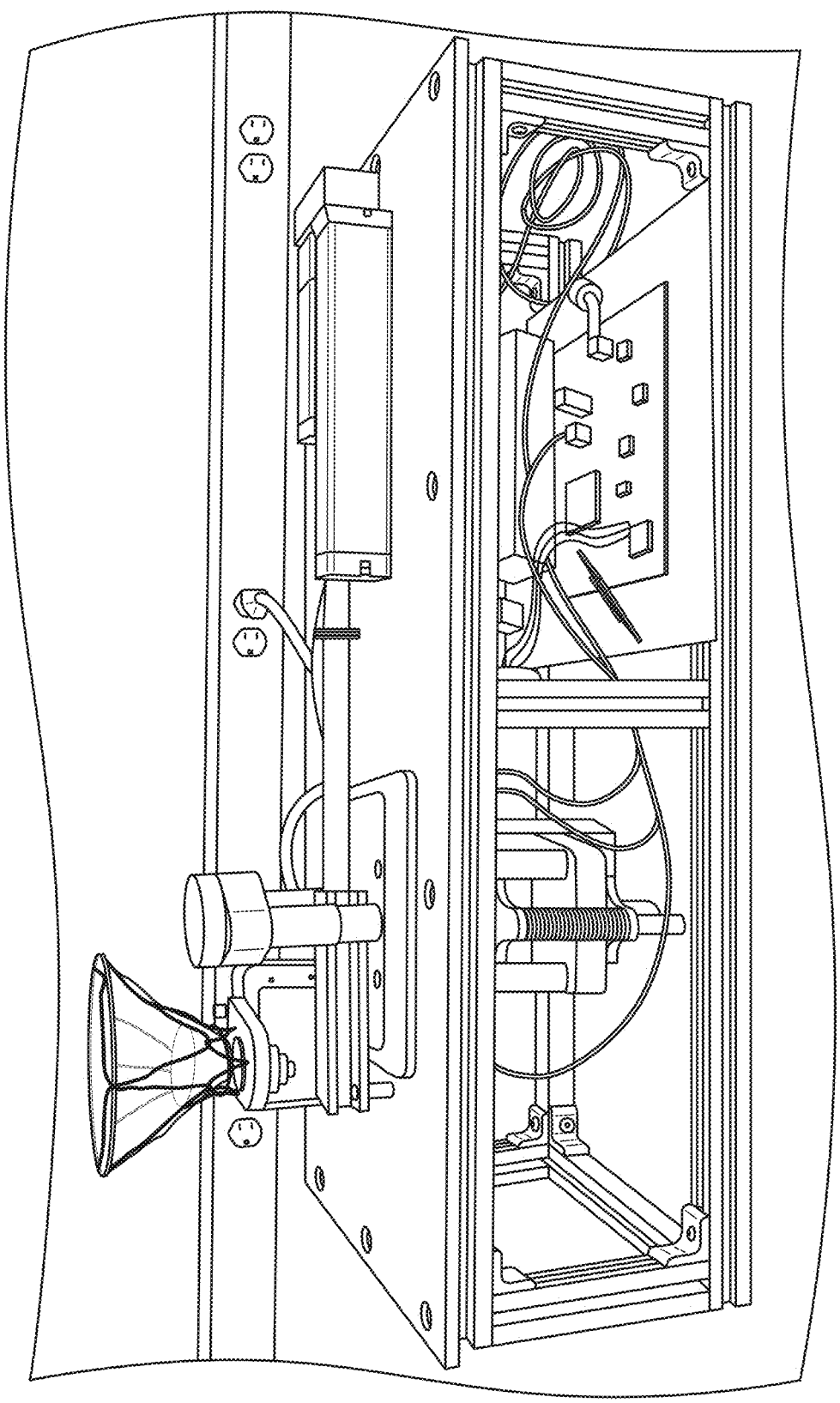
FIG. 17 depicts a lower stream process arrangement.

The lower process stream will now be discussed. FIGS. 16 and 17 depict one illustrative embodiment of a lower process stream, including a dispenser 210 and a tableting unit (which may include, in part, a tablet die 231 and a tablet punch 232).

In some embodiments, a second dispensing step is used to dispense the mixed blend into smaller, discrete portions of material that are each ultimately compressed to form a single tablet.

Figure 18:
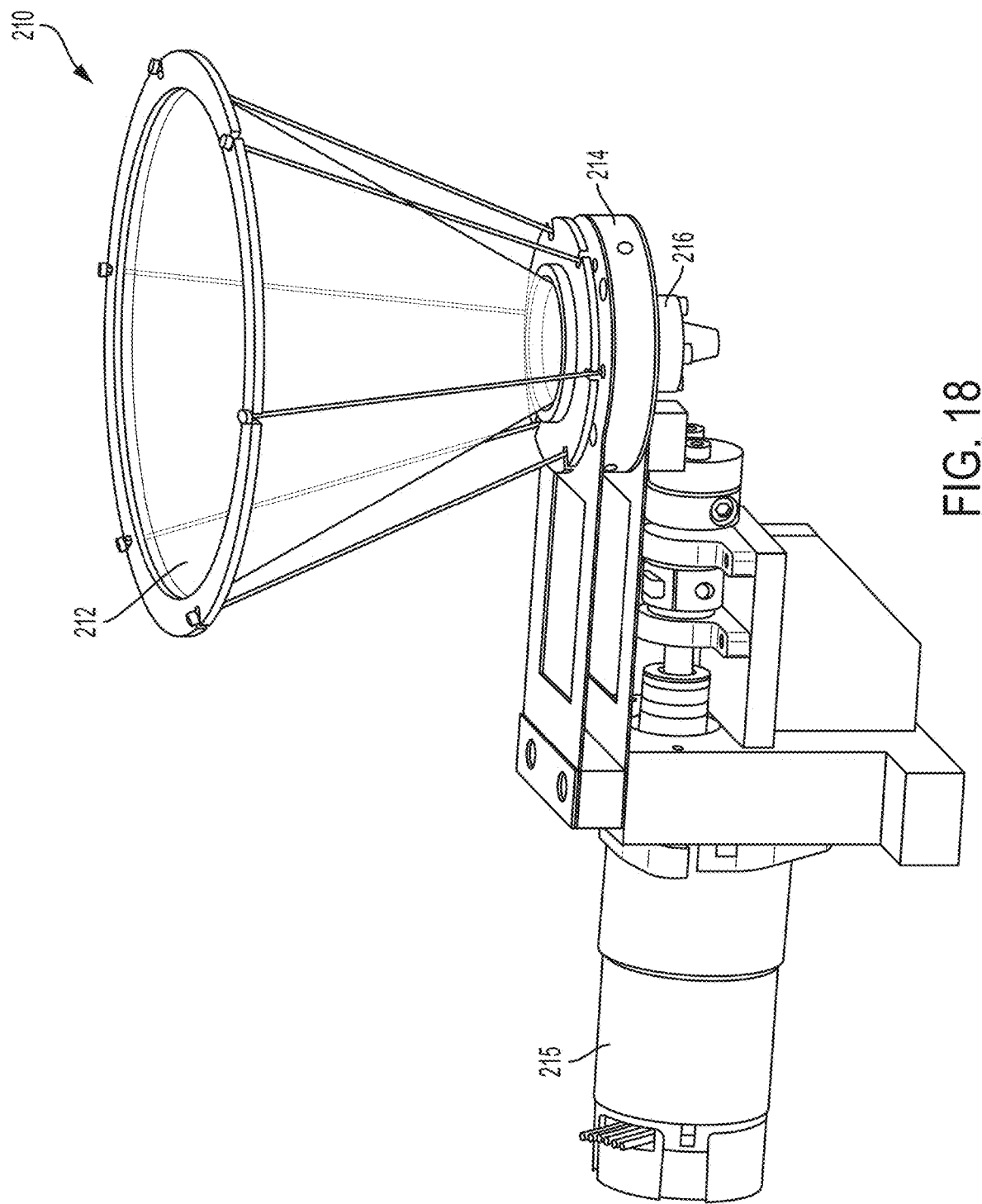
FIG. 18 is a perspective view of a mixed blend dispenser according to one set of embodiments.
Figure 19:
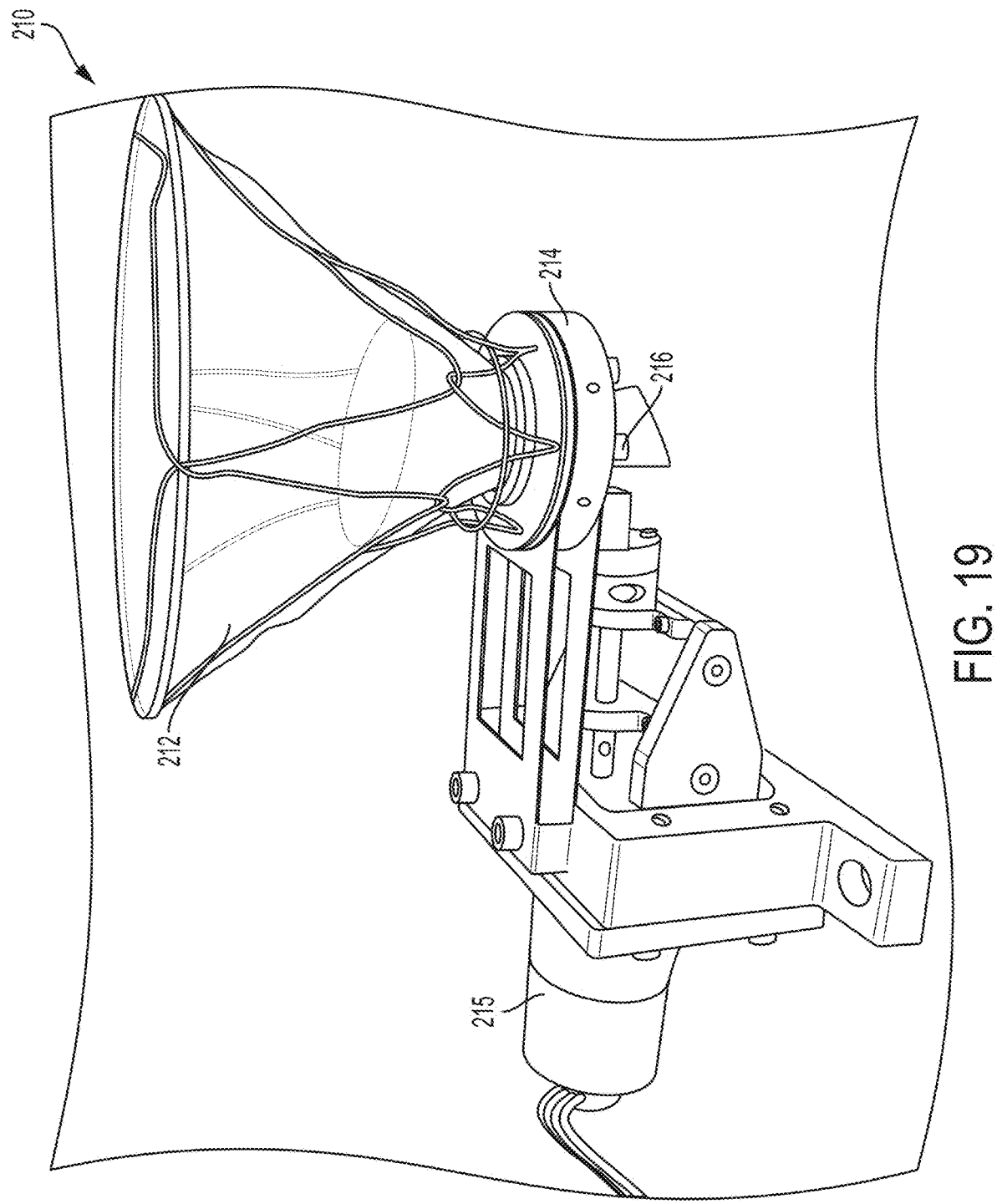
FIG. 19 depicts a mixed blend dispenser.

In one illustrative embodiment shown in FIGS. 18 and 19, blended mix dispenser 210 includes a hopper 212, a mechanical vibration unit 214 and a dispense head 216. The blended mix from the blender 130 sits within the hopper 212. In some embodiments, the vibration unit 214 operates based on a tapping mechanism in which an actuator 215 causes the vibration unit to move up and down. In some embodiments, the tapping mechanism includes a mallet or other device that strikes the hopper itself or a component that is in contact with the hopper, causing the hopper to move up and down. The dispense head 216 may include one or more holes. Up and down movement of the hopper may cause material to exit the hole(s) of the dispense head 216. Without wishing to be bound by theory, the tapping mechanism may build powder micro-bridges which break down on impact and then re-build.

Figure 20A:
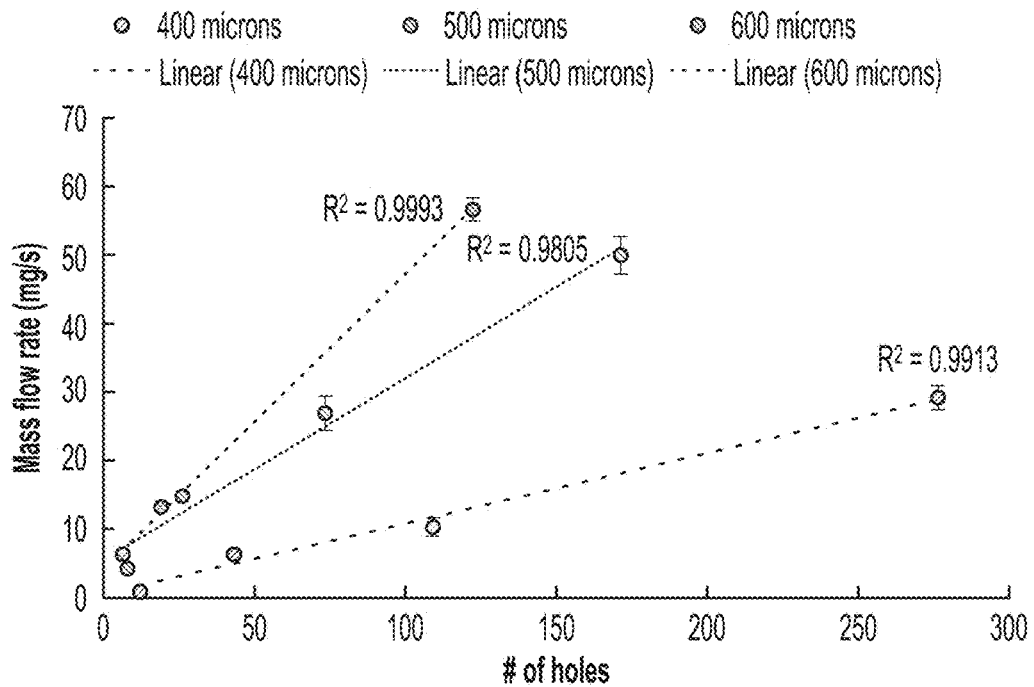
FIGS. 20A-B depict graphs indicating dispenser performance.
Figure 20B:
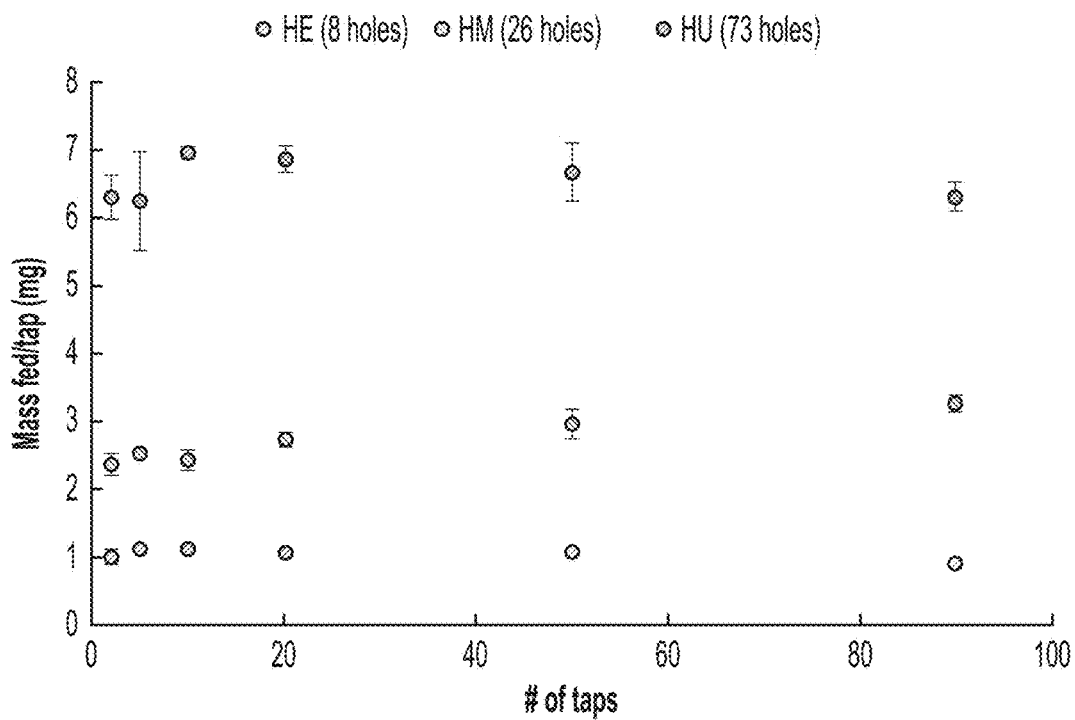

Dispense performance of the dispenser was tested using dispense heads of different hole sizes. As seen in the test results depicted in FIG. 20A, a linear relationship was observed with mass flow rate and number of holes. As seen in the test results depicted in FIG. 20B, measurements of mass fed per tap (i.e. mass dispensed per tap) were found to be sufficiently consistent, and increased with an increase in the number of holes in the dispense head.

It should be appreciated that other dispensing mechanisms may be used, such as those enumerated above with regard to the API and excipient dispensers upstream from the blender.

In some embodiments, the tableting process comprises a direct compaction method in which powder (e.g., API powder and/or excipient powder) and/or other tablet ingredients are pressed into the final tablet shape. In some embodiments, the tableting assembly may include a tablet die and a tablet punch that cooperate to create tablets. The punch may be lowered into the tablet die to compact tablet ingredients to form a tablet. In some embodiments, the tableting assembly may also include a die actuator that moves the die from a receiving position in which it receives a discrete amount of blended mix from the blended mix dispenser 210 to a compaction position in which it is aligned with the tablet punch. In some embodiments, the die actuator may also move the die to an ejection position in which the completed tablet is ejected from the die.

In some embodiments, the system may include different tablet die sizes and punches depending on the tablet dosage size. The system may switch between different die and punch sizes automatically, or may require a manual adjustment.

In some embodiments, after the tablet is formed and ejected, it is weighed by a weigh scale to determine whether or not the tablet has the desired amount of mass. If the weigh scale determines that the tablet does not satisfy mass requirements, the system may reject and discard the tablet.

Figure 21:
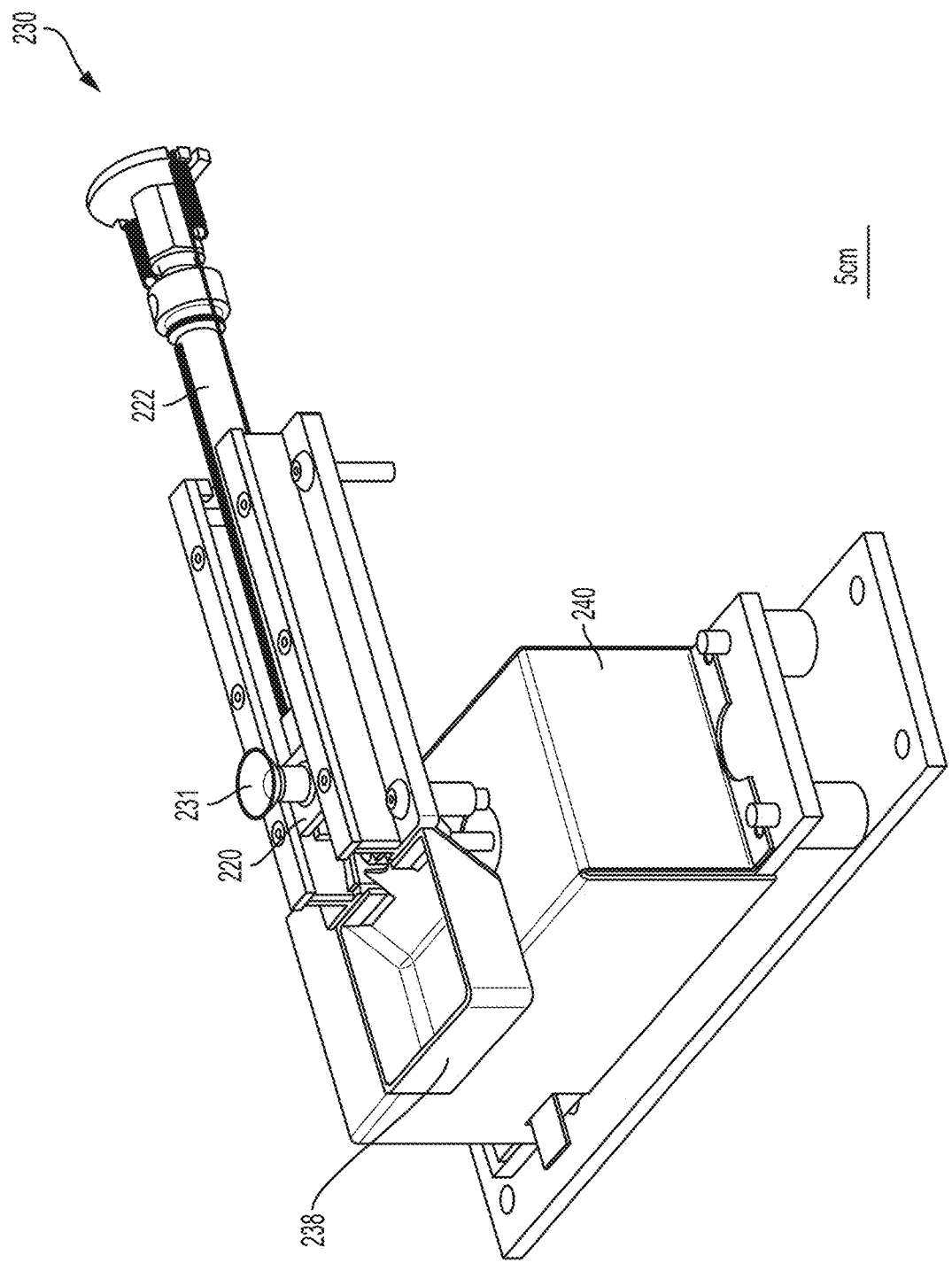
FIG. 21 is a perspective view of a tableting unit and weigh scale according to one set of embodiments.

One illustrative embodiment of a tableting unit 230 is shown in FIG. 16, and a portion of the tableting unit is shown in FIG. 21 (the tablet punch 232 is omitted in FIG. 21). In some embodiments, the tableting unit 230 may include a tablet die 231, a die carriage 220 (best seen in FIG. 21), a die actuator 222 and a tablet punch 232.

In some embodiments, first, powder is dispensed into the tablet die 231 from the blended mix dispenser 210. A die actuator 222 may move the tablet die 231 and the die carriage 220 until the die 231 is positioned below the tablet punch 232 (the die carriage 220 is best seen in FIG. 21). A press 233 associated with the tablet punch 232 is seen in FIG. 5. In some embodiments, a GAMLEN tableting press, punch and die (Gamlen, Nottingham UK) may be used.

In some embodiments, with the tablet die 231 and the tablet punch 232 aligned, the tablet punch 232 is lowered into the tablet die 231 and compacts the tablet ingredients within the die 231 to form a tablet. In FIG. 16, for example, the tablet punch 232 and tablet die 231 are shown in the aligned position. In some embodiments, the formed tablet is then ejected into the tablet output tray 238.

In some embodiments, the tablet punch is configured to apply varying amounts of compaction pressure depending on hardness requirements, the tablet formulation, and/or tablet size. In some embodiments, the controller may communicate to the tablet punch the appropriate compaction pressure to apply. In some embodiments, one or more sensors such as transducers (e.g., piezoelectric transducers) may be used to monitor and/or control tablet press compaction pressure. For example, in some embodiments, one or more sensors may be located within the tablet punch and/or the tablet die during compaction.

In some embodiments, such as the embodiment shown in FIG. 5 and FIG. 21, a weigh scale 240 may be used to determine the weight of each formed tablet. In some embodiments, the tablet output tray 238 is positioned on the weigh scale, and the weigh scale detects the weight of each formed tablet by detecting the change in weight each time a tablet is output in the tray.

Figure 22:
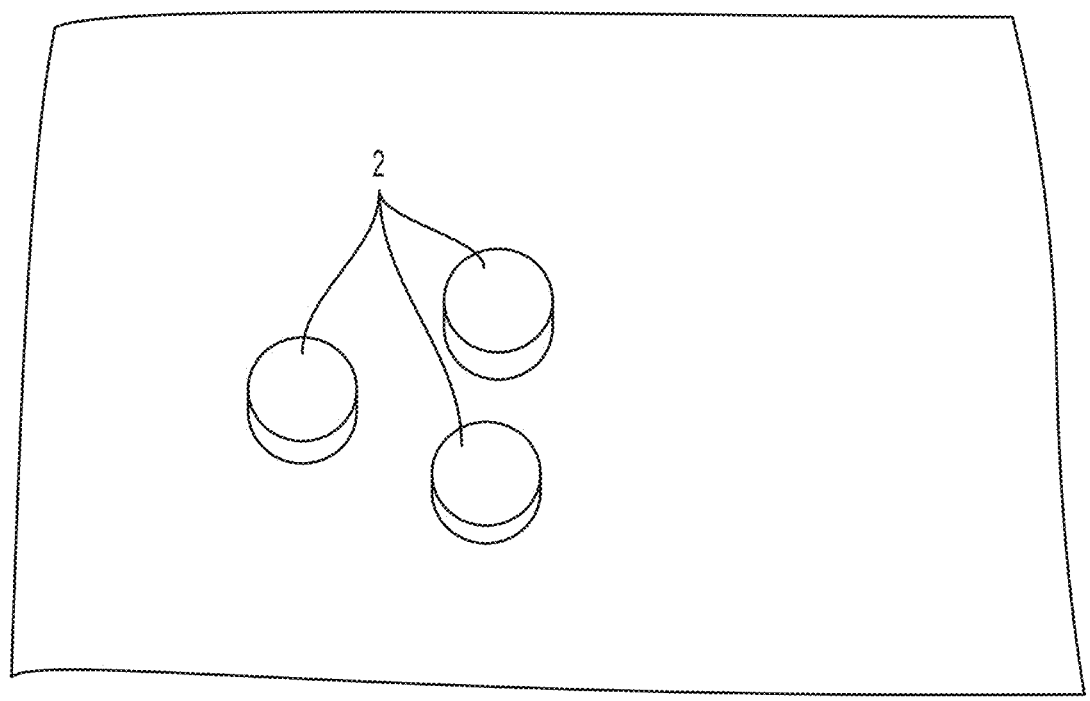
FIG. 22 depicts tablets produced by the tableting unit.

In some embodiments, if the tablet is measured to be of the expected weight for the tablet, the tablet is retained, and if the tablet is not of the expected weight, the tablet is discarded. An example of resulting tablets 2 produced by a tablet production system is shown in FIG. 22.

In some embodiments, the tableting unit requires only an upper punch 232, and does not require a lower punch. However, in other embodiments, a lower punch may be used.

In some embodiments, techniques described herein may be carried out using one or more computing devices, including, but not limited to, network databases, storage systems, and central plant controllers. For example, the system may include a controller that includes one or more computing devices. Embodiments are not limited to operating with any particular type of computing device.

Figure 23:
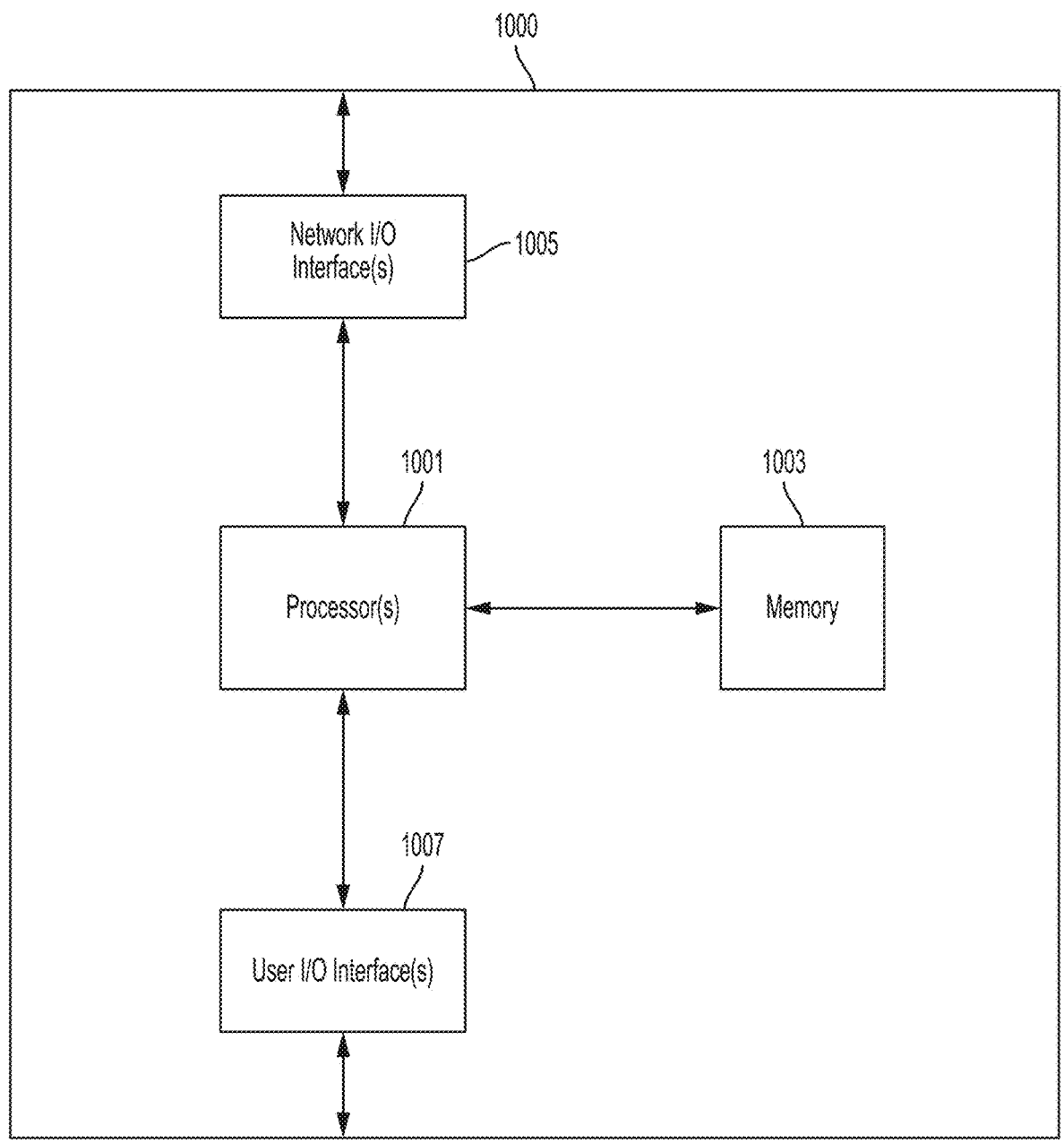
FIG. 23 is a block diagram of an illustrative computing device that may be used to implement a method of producing pharmaceutical tablets.

FIG. 23 is a block diagram of an illustrative computing device 1000 that may be used to implement any of the above-described techniques. Computing device 1000 may include one or more processors 1001 and one or more tangible, non-transitory computer-readable storage media (e.g., memory 1003). Memory 1003 may store, in a tangible non-transitory computer-recordable medium, computer program instructions that, when executed, implement any of the above-described functionality. Processor(s) 1001 may be coupled to memory 1003 and may execute such computer program instructions to cause the functionality to be realized and performed.

Computing device 1000 may also include a network input/output (I/O) interface 1005 via which the computing device may communicate with other computing devices (e.g., over a network), and may also include one or more user I/O interfaces 1007, via which the computing device may provide output to and receive input from a user. The user I/O interfaces may include devices such as a keyboard, a mouse, a microphone, a display device (e.g., a monitor or touch screen), speakers, a camera, and/or various other types of I/O devices.

The above-described embodiments can be implemented in any of numerous ways. For example, the embodiments may be implemented using hardware, software or a combination thereof. When implemented in software, the software code can be executed on any suitable processor (e.g., a microprocessor) or collection of processors, whether provided in a single computing device or distributed among multiple computing devices. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above. In some embodiments, a combination of programmable hardware and dedicated hardware may also be used.

In this respect, it should be appreciated that one implementation of the embodiments described herein comprises at least one computer-readable storage medium (e.g., RAM, ROM, EEPROM, flash memory or other memory technology, CD-ROM, digital versatile disks (DVD) or other optical disk storage, magnetic cassettes, magnetic tape, magnetic disk storage or other magnetic storage devices, or other tangible, non-transitory computer-readable storage medium) encoded with a computer program (i.e., a plurality of executable instructions) that, when executed on one or more processors, performs the above-discussed functions of one or more embodiments. The computer-readable medium may be transportable such that the program stored thereon can be loaded onto any computing device to implement aspects of the techniques discussed herein. In addition, it should be appreciated that the reference to a computer program which, when executed, performs any of the above-discussed functions, is not limited to an application program running on a host computer. Rather, the terms computer program and software are used herein in a generic sense to reference any type of computer code (e.g., application software, firmware, microcode, or any other form of computer instruction) that can be employed to program one or more processors to implement aspects of the techniques discussed herein.

According to one aspect, the tablets may be created on-demand, e.g., a user may input an instruction to the system specifying the desired dosage and/or desired drug type. In response, the system will dispense the appropriate type and amount of API and excipient in accordance with the user's instruction. In some embodiments, the system may include a controller that receives the user's instructions and controls the system components to carry out the instructions.

For example, the system may receive instructions to produce 100 tablets of ibuprofen having a dosage of 500 mg and 50 tablets of ibuprofen having a dosage of 100 mg. The system controller receives the instructions and commands the various components of the system to produce tablets accordingly. For example, in some embodiments, the controller may instruct the blended mix dispenser (the dispenser downstream from the blender) to dispense a suitable mass of the mixed blend for the 500 mg tablets 100 times, and then dispense a suitable mass of the mixed blend for the 100 mg tablets 50 times. In this manner, in some embodiments, the system may seamlessly switch from production of a first tablet dosage to a second tablet dosage of the same drug without the need for production pauses or disconnecting/connecting modules or unit operations.

As another example, the system may receive instructions to produce 100 tablets of a first drug type (e.g., ibuprofen) and 50 tablets of a second, compositionally different drug type (e.g., azithromycin). The system controller receives the instructions and commands the various components of the system to produce tablets accordingly. In some embodiments, the dispensers upstream from the blender may already include all of the APIs and excipients required for both drugs. For example, three dispensers may hold the API(s) and excipient(s) required to make the first drug type, and three other dispensers may hold the API(s) and excipients required to make the second drug type. In other embodiments, the dispensers holding the ingredients needed for the second drug type are not connected to the system until after production of the first drug type has finished.

In some embodiments, when switching between production of different drug types, the "touch points" of the system may be replaced with clean components. Touch points of the system include any component of the system that came into contact with dispensed tablet ingredients (e.g., API or excipients). Examples of touch points include the carriage, blender impeller and mixing vessel, the blended mix dispenser hopper, the tablet die, the tablet press, and the tablet output tray. These components may be swapped out automatically by the system, manually by an operator, or a mix of both. However, production of both types of drug may still be considered to be run on the same physical system, as the overall infrastructure the system has not changed. For instance, the frames to which components are coupled may remain the same, the weigh scale and the actuator moving the carriage may remain the same, the blender motor and actuator may remain the same, the blended mix dispenser actuator may remain the same, and/or the tablet die actuator may remain the same.

Figure 24:
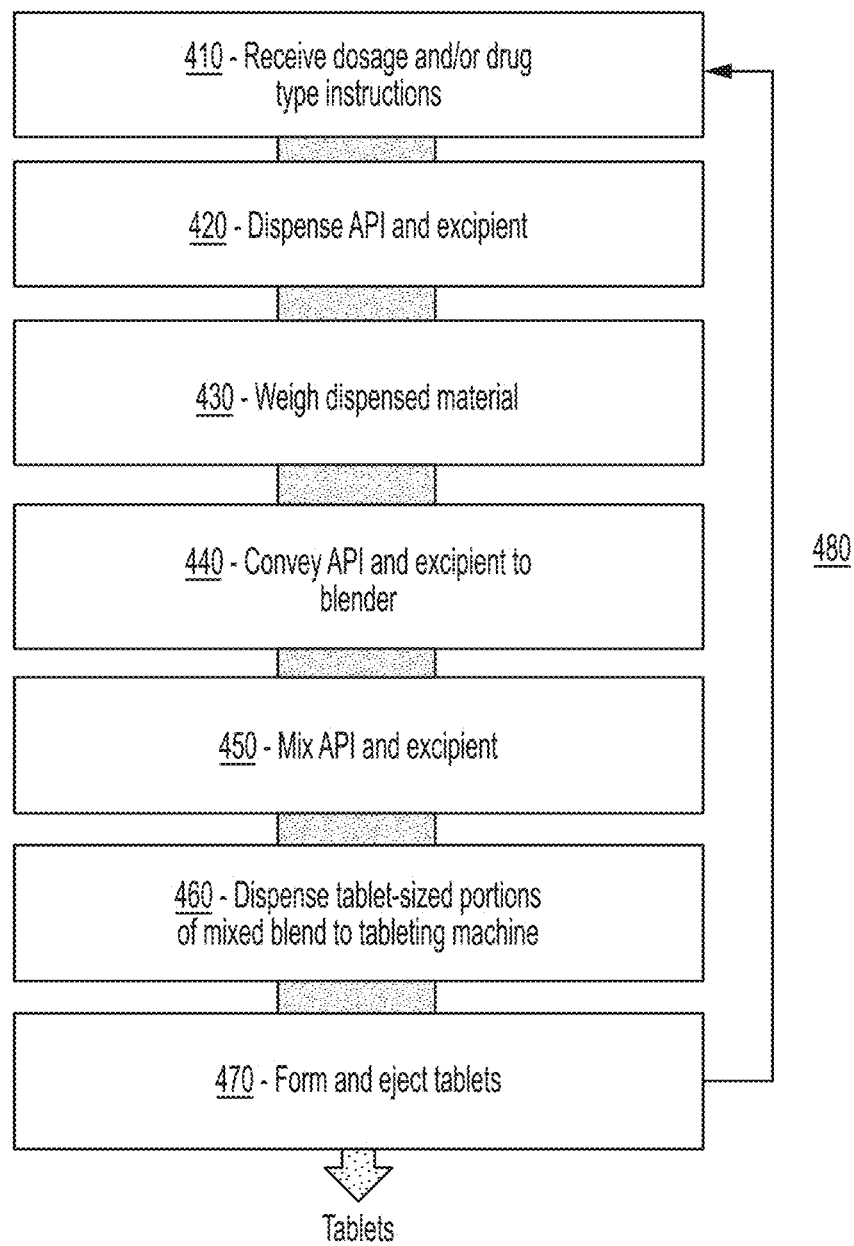
FIG. 24 is a block diagram of a method of producing pharmaceutical tablets.

A schematic flow chart of one such process according to one embodiment is shown in FIG. 24. First, the system receives dosage and/or drug type instructions 410. Such instructions may be input by a user, e.g., a user interacting with a control panel of the system, a user sending instructions from a remote location, etc. In some embodiments, the system may be pre-programmed with instructions. In response to the instructions, the system dispenses 420 the appropriate API(s) and excipient(s) needed to make the specified drug type. The dispensed material is weighed 430 and conveyed 440 to a blender. The blender creates a mixed blend 450, and a dispenser dispenses appropriately-sized portions of the mixed blend to satisfy the specified dosage 460. The tableting machine then receives material from the dispenser and forms and ejects tablets 470. Step 480 indicates that, if new instructions are received, the cycle restarts.

In some embodiments, at least one of the dispensing, blending and tableting steps are carried out at least partially in response to the instructions.

As noted above, certain of the systems and methods described herein include the use of an active pharmaceutical ingredient ("API"). As used herein, the term "active pharmaceutical ingredient" refers to an agent that is administered to a subject to treat a disease, disorder, or other clinically recognized condition, or for prophylactic purposes, and has a clinically significant effect on the body of the subject to treat and/or prevent the disease, disorder, or condition. Active pharmaceutical ingredients include, without limitation, agents listed in the United States Pharmacopeia (USP), Goodman and Gilman's The Pharmacological Basis of Therapeutics, 10th Ed., McGraw Hill, 2001; Katzung, B. (ed.) Basic and Clinical Pharmacology, McGraw-Hill/Appleton & Lange, 8th edition (Sep. 21, 2000); Physician's Desk Reference (Thomson Publishing); and/or The Merck Manual of Diagnosis and Therapy, 17th ed. (1999), or the 18th ed (2006) following its publication, Mark H. Beers and Robert Berkow (eds.), Merck Publishing Group, or, in the case of animals, The Merck Veterinary Manual, 9th ed., Kahn, C. A. (ed.), Merck Publishing Group, 2005. Preferably, though not necessarily, the active pharmaceutical ingredient is one that has already been deemed safe and effective for use in humans or animals by the appropriate governmental agency or regulatory body. For example, APIs approved for human use are listed by the FDA under 21 C.F.R. §§ 330.5, 331 through 361, and 440 through 460, incorporated herein by reference; APIs for veterinary use are listed by the FDA under 21 C.F.R. §§ 500 through 589, incorporated herein by reference. All listed APIs are considered acceptable for use in accordance with the present invention.

In certain embodiments, the active pharmaceutical ingredient is a small molecule. Exemplary active pharmaceutical ingredients include, but are not limited to, anti-cancer agents, antibiotics, anti-viral agents, anesthetics, anti-coagulants, inhibitors of an enzyme, steroidal agents, steroidal or non-steroidal anti-inflammatory agents, antihistamine, immunosuppressant agents, antigens, vaccines, antibodies, decongestant, sedatives, opioids, pain-relieving agents, analgesics, anti-pyretics, hormones, prostaglandins, etc.

As used herein, the term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is at most about 1,000 g/mol, at most about 900 g/mol, at most about 800 g/mol, at most about 700 g/mol, at most about 600 g/mol, at most about 500 g/mol, at most about 400 g/mol, at most about 300 g/mol, at most about 200 g/mol, or at most about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and at most about 500 g/mol) are also possible.

Non-limiting examples of APIs include diphenhydramine, ciprofloxacin, diazepam, fluoxetine, ibuprofen, doxycycline, and azithromycin. Those of ordinary skill in the art, given the present disclosure, would be capable of applying the synthesis methods and systems described herein to other pharmaceutical active ingredients.

Also as noted above, certain of the systems and methods described herein can be used to produce ingestible pharmaceutical compositions. Generally, ingestible pharmaceutical compositions refer to those compositions including an active pharmaceutical ingredient and a pharmaceutically acceptable excipient. As used herein, the term "pharmaceutically acceptable excipient" means a non-toxic, inert solid, semi-solid or liquid filler, diluent, encapsulating material or formulation auxiliary of any type. Some non-limiting examples of materials which can serve as pharmaceutically acceptable excipients are sugars such as lactose, glucose, and sucrose; starches such as corn starch and potato starch; cellulose and its derivatives such as sodium carboxymethyl cellulose, methylcellulose, hydroxypropylmethylcellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; water (e.g., pyrogen free water); isotonic saline; citric acid, acetate salts, Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Other possible excipients include glidant and solubilizer.

In some embodiments, the ingestible pharmaceutical composition comprises at least about 2.5 mg, at least about 5.0 mg, or at least about 20 mg of an active pharmaceutical ingredient per milliliter of a pharmaceutically acceptable excipient. In some embodiments, the active pharmaceutical ingredient is dissolved in the pharmaceutically acceptable excipient. In certain embodiments, the active pharmaceutical ingredient is suspended in the pharmaceutically acceptable excipient. In some embodiments, the ingestible pharmaceutical composition is in the form of a tablet.

In some embodiments, the system is configured to produce at least about 1000 doses of API per day. In certain embodiments, the system is configured to produce at least about 2000 doses per day, at least about 4000 doses per day, at least about 8000 doses per day, at least about 10000 doses per day, or at least about 20000 doses per day. As will be generally understood by one skilled in the art, the term dose generally refers to an amount of an active pharmaceutical ingredient which is administered to an organism (e.g., a person, an animal, a plant, an insect, and/or a bacterium) to stimulate a biological response. In certain embodiments, the system is configured to produce at least about 20 grams/day, at least about 50 grams/day, at least about 100 grams/day, at least about 200 grams per day, or at least about 400 grams per day of an ingestible pharmaceutical composition.

In certain embodiments, the system is configured to produce a relatively high amount of an active pharmaceutical ingredient in a small footprint. For example, in some cases, the system may be configured to produce at least about 5 grams of an active pharmaceutical ingredient per square foot footprint area per day. In some embodiments, the system is configured to produce at least about 7 $g/day/ft^2$, at least about 10 $g/day/ft^2$, at least about 20 $g/day/ft^2$, at least about 30 $g/day/ft^2$, at least about 50 $g/day/ft^2$, at least about 60 $g/day/ft^2$, at least about 70 $g/day/ft^2$, at least about 90 $g/day/ft^2$, at least about 100 $g/day/ft^2$, at least about 120 $g/day/ft^2$, at least about 150 $g/day/ft^2$, or at least about 200 $g/day/ft^2$ of an active pharmaceutical ingredient per day per footprint area. In certain embodiments, the system is configured to produce at least about 1 gram of an active pharmaceutical ingredient per cubic feet of a housing (e.g., as described above) per day. For example, in some embodiments, the system is configured to produce at least about 2 $g/day/ft^3$, at least about 3 $g/day/ft^3$, at least about 4 $g/day/ft^3$, at least about 5 $g/day/ft^3$, at least about 7 $g/day/ft^3$, at least about 10 $g/day/ft^3$, at least about 15 $g/day/ft^3$, at least about 20 $g/day/ft^3$, or at least about 25 $g/day/ft^3$ of an active pharmaceutical ingredient per volume of a housing per day.

Example

A tableting system for producing pharmaceutical tablets was used to manufacture ibuprofen (IBU) and diazepam (DIZ) tablets.

The system was divided into an upper process stream and lower process stream. The upper process stream began with individual powder (API and excipients) feeding and ended with blending. The lower process stream began with dispensing of the powder blend to the compression of tablets. A direct compression method was used to make the tablets. These two process streams operated independently under high-level software control.

The dimensions of the system measure approximately 72.4 cm (length) by 53.3 cm (width) by 134.6 cm (height). API and excipients were fed from multiple volumetric feeders to a carriage consisting of a boat suspended from a load cell. The feeders were modified to dispense cohesive APIs and excipients, when necessary. The carriage could be commanded to move to any volumetric feeder, in any sequence, and the required amounts of powder may be dispensed at each feeder location. The carriage transferred powder (any number of transfers may be possible) from the boat to a conical blender with an impeller. The blender mixed powder via convective mixing to achieve a blend. After mixing, the blend was dispensed into the hopper of a blended mix dispenser having a tapping feeder. CAPSUGEL (South Carolina, USA) dispense heads were used on the tapping feeder to regulate the amount of powder fed. Powder was then dispensed in pre-determined amounts (depending on the desired dosage size) into a tablet press die. The actuator would slide the die into position underneath the actuated punch of a laboratory tablet press (Gamlen PCA-500D, Gamlen Tableting Ltd, UK). The blend was then compressed to make the tablet. The tablet was ejected from the die, then transferred to a weighing station. Finally, the tablet was collected.

The materials used for making the ibuprofen and diazepam tablets, along with their specific functions, are presented in Table 1 below.

TABLE 1

Materials used for making tablets and their functionality.

| Material | Trade name/CAS number* | Functionality | Manufacturer/supplier |
|---|---|---|---|
| Ibuprofen (IBU) | 15687-27-1 | Drug/API | Spectrum Chemical Mfg. Corp. |
| Diazepam (DIZ) | 439-14-5 | Drug/API | Sigma Aldrich |
| Anhydrous lactose | SuperTab ® 21AN | Filler/Diluent | DFE Pharma |
| Fumed silica | CAB-O-SIL ® M-5P | Glidant/Flow aid | Cabot Corporation |
| Magnesium stearate NF/EP/JP | Kosher Passover HyQual ™ | Lubricant | Mallinckrodt Pharmaceuticals |

*Chemical Abstracts Service (CAS)

Physical properties of ibuprofen and diazepam APIs are presented in Table 2 below.

TABLE 2

Physical properties of Active Pharmaceutical Ingredients (APIs) studied.

| APIs | Function | Molecular weight g/mol | Solubility in water (mg/ml) |
|---|---|---|---|
| Ibuprofen (IBU) | Anti-inflammatory | 206.285 | 0.021 |
| Diazepam (DIZ) | Anxiolytic and sedative | 284.743 | 0.050 |

TABLE 3

Formulations used for making IBU and DIZ tablets.

|  | IBU | DIZ |
|---|---|---|
| Tablet properties |  |  |
| API strength (mg) | 200 | 10 |
| Tablet weight (mg) | 340 | 250 |
| Tablet formulation compositions (%) |  |  |
| API | 58.82 | 4.00 |
| Anhydrous lactose | 40.18 | 95.00 |
| Fumed silica | 0.50 | 0.50 |
| Magnesium stearate | 0.50 | 0.50 |
|  | 100.00 | 100.00 |
| Blend formulation compositions (g) |  |  |
| API | 30.59 | 1.74 |
| Anhydrous lactose | 20.89 | 41.42 |
| Fumed silica | 0.26 | 0.22 |
| Magnesium stearate | 0.26 | 0.22 |
|  | 52.00 | 43.60 |

The particle sizes of the API and excipients, except fumed silica, are presented in Table 4 below.

TABLE 4

Properties of Active Pharmaceutical Ingredients (APIs) and excipients used for tableting.

| API, Excipients | Particle size (μm) | | | Bulk density g/cm$^3$ | Compressibility (%) | Flow function coefficient (ffc) |
|---|---|---|---|---|---|---|
|  | $d_{10}$ | $d_{50}$ | $d_{90}$ |  |  |  |
| Ibuprofen (IBU) | 4.86 | 21.87 | 75.31 | 0.53 | 25.07 | 3.87 |
| Diazepam (DIZ) | 5.74 | 23.12 | 110.75 | 0.52 | 32.73 | 2.78 |
| Anhydrous lactose | 26.03 | 188.75 | 425.90 | 0.74 | 13.10 | 5.69 |
| Magnesium stearate | 2.76 | 6.86 | 15.10 | 0.31 | 38.97 | 5.18 |

A simplified approach in formulation development was considered by minimizing number of excipients required for tableting. Hence, only one filler/diluent, flow aid/glidant and lubricant were considered as part of the formulations for both model drugs. Anhydrous lactose (SuperTab® 21AN) was used as the filler/diluent, fumed silica (CAB-O-SIL® M-5P) was used as the glidant, and magnesium stearate (Kosher Passover HyQual™) was used as the lubricant. This grade of anhydrous lactose was selected as the filler in the formulations.

The formulated blends were used for the manufacturing of tablets. The compositions of the formulations used are presented in Table 3 below.

Figure 29A:
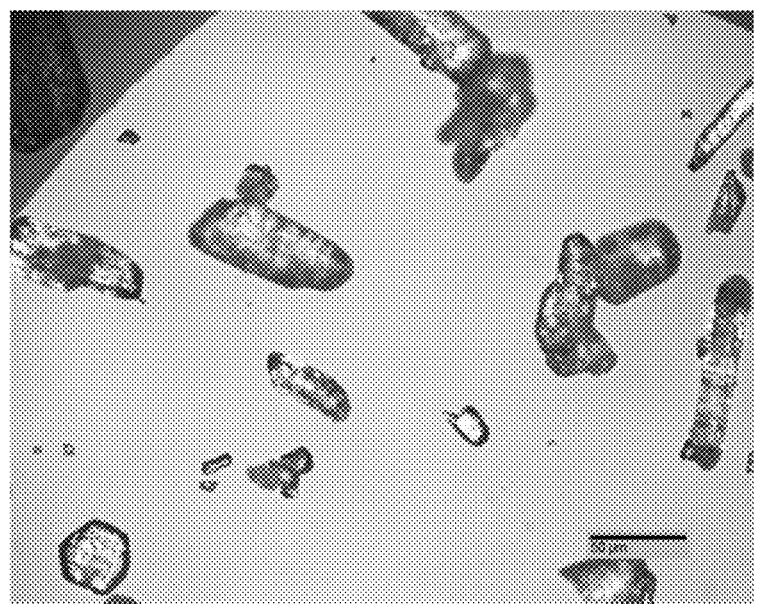
FIG. 29A is an optical microscope image of ibuprofen particles used in a tableting process.
Figure 29B:
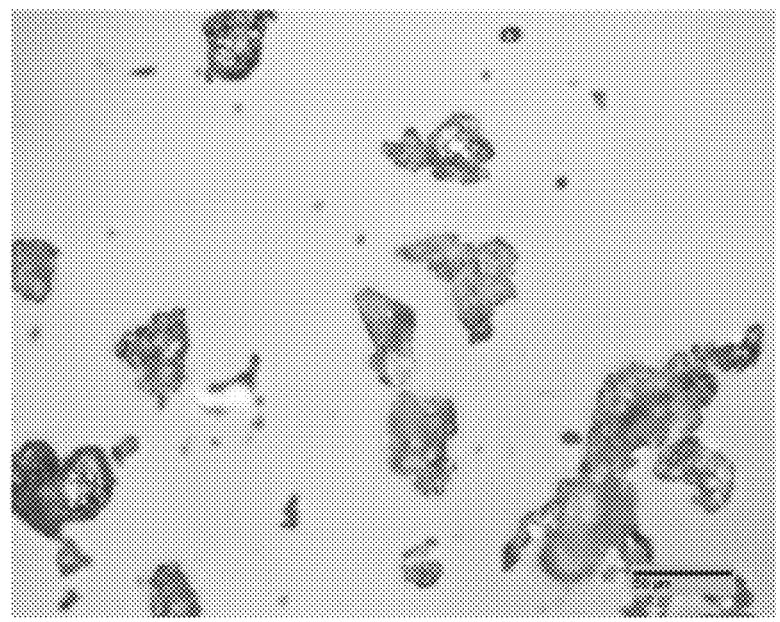
FIG. 29B is an optical microscope image of diazepam particles used in a tableting process.

Microscopy images showing the morphology of IBU and DIZ particles are shown in FIGS. 29A and 29B, respectively. Particle and bulk properties of IBU and DIZ are summarized in Table 4 above. IBU and DIZ both are fine particles with a $d_{50}$ of 21.87 μm and 23.12 μm, respectively. The microscopy image shows IBU as plate-like rectangular shape particles (FIG. 29A), whereas DIZ particles are irregular shaped, agglomerated particles (FIG. 29B).

Flow properties of powder blends prepared for tablets were measured using FT4 Powder Rheometer and are presented in Table 5 below.

TABLE 5

Properties of powder blends prepared for tableting.

| Blends | Bulk density g/cm³ | Compressibility (%) | Flow function coefficient (ffc) |
|---|---|---|---|
| Ibuprofen (IBU) | 0.65 | 5.18 | >10 |
| Diazepam (DIZ) | 0.72 | 12.27 | >10 |

Lactose, API, and silica were fed consecutively into the blender for IBU blending. Lactose was split into two equal quantities for DIZ blend. Half was fed into blender at the beginning and the remaining half was fed the end of feeding sequence. The blender was operated at 80 RPM and blended all materials for 26 minutes. Then magnesium stearate was added into the blender and blended for an additional 4 minutes at 80 RPM. The magnesium stearate was not added at the beginning to prevent over-lubrication of the formulation. A total of 52.0 g of IBU blend and a total of 43.6 g of DIZ blend were produced in each blend batch. 40% of the total blender volume was used for blending based on the measured conditioned bulk density of each final blend.

Figure 30:
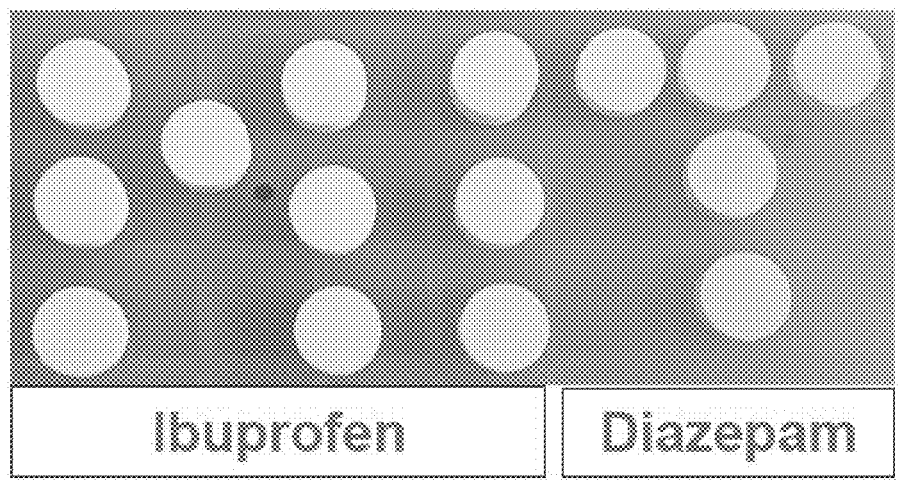
FIG. 30 depicts ibuprofen and diazepam tablets manufactured using a system for producing pharmaceutical tablets.

The final blend was transferred into the tapping feeder hopper. The powder was dispensed into a 10 mm die to make tablets of 340 mg and 250 mg total weight for IBU and DIZ, respectively. The number of taps required to obtain the necessary fill weight was 53 (±5) for IBU and 35 (±5) for DIZ. The accepted weight variation was considered ±10% of target tablet weight. Dispensed powder was compressed at a force of 450 kg to make tablets using a flat and round punch with a diameter of 10 mm. The punch speed was programmed at 1.0 mm/s. Each tablet was weighed and its dimensions (diameter and thickness) were measured using a digital slide caliper (Fowler 54-100-000-2, Fowler Company Inc., Newton, Mass.). Twenty-two tablets for IBU and forty-two tablets for DIZ were manufactured and analyzed. Some of the manufactured ibuprofen and diazepam tablets are shown in FIG. 30.

Properties of the resulting manufactured IBU and DIZ tablets were measured (weight, tensile strength, assay, and content uniformity) and are presented in Table 6 below.

TABLE 6

Properties of tablets (weight, tensile strength, assay and acceptance value) prepared using blends.

| Blends | Tablet weight (Average, % RSD) (mg) | Tensile strength (Average ± STDEV) MPa | Assay (% of the labeled content) (%) | Acceptance value (AV) |
|---|---|---|---|---|
| Ibuprofen (IBU) | 334.07, 2.58 | 1.14 ± 0.09 | 98.81 | 6.12 |
| Diazepam (DIZ) | 258.06, 2.99 | 0.52 ± 0.07 | 103.69 | 9.36 |

The average weight of 10 tablets manufactured are reported with % RSD value. The average weight of IBU and DIZ were 334.07 mg and 258.06 mg, respectively. The weight variation was within the ±10% of target tablet weight 340 mg for IBU and 250 mg for DIZ. The RSD value was below 3% for both drug tablets. The low RSD indicates uniform dispense of blend into the die and low weight variation among tablets.

The average tensile strength of IBU and DIZ tablets were 1.14 MPa and 0.52 MPa, respectively. The diameter and thickness of six tablets were measured. For IBU tablets, the average values for diameter and thickness were 10.06 (±0.03) mm and 3.8 (±0.12) mm, respectively. For DIZ tablets, the average values for diameter and thickness were 10.11 (±0.02) mm and 2.59 (±0.06) mm, respectively.

According to USP-39, official monograph IBU/DIZ tablets must contain not less than 90% and not more than 110% of the labeled amount meet the assay standard. Similarly, if the calculated acceptance value of the active ingredient, based on 10 dosage units, is less than or equal to 15.0, then the product meets the USP quality standard. As shown in Table 6, the assay values of the IBU and DIZ tablets are within the range of 90-110%. Both the IBU and DIZ tablets meet the content uniformity/weight variation criteria, as the acceptance value (AV) is below 15.

Figure 31A:
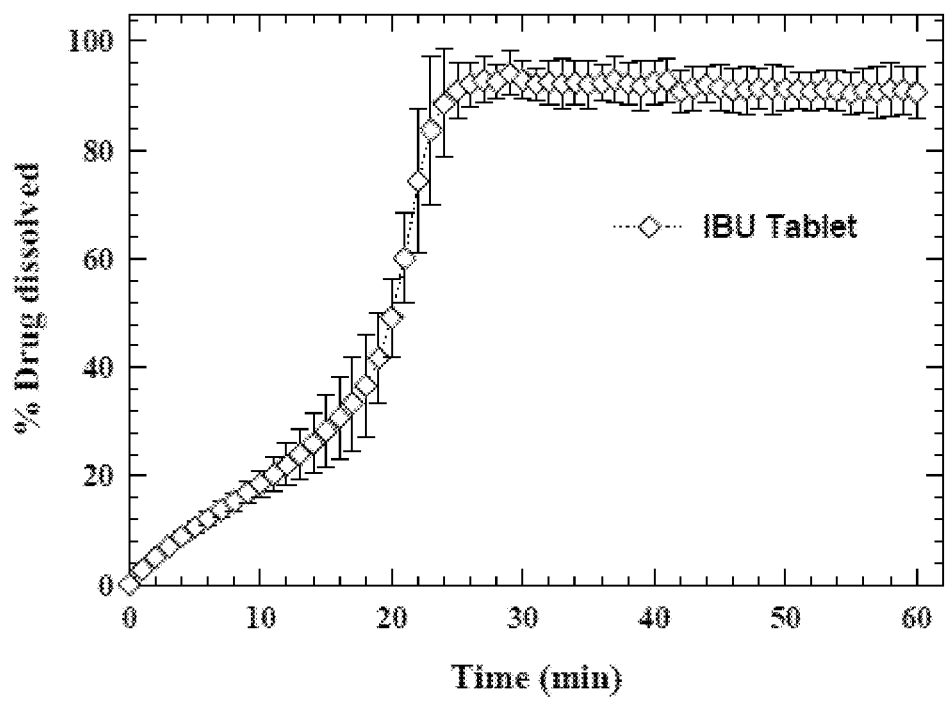
FIG. 31A illustrates the dissolution results for the manufactured ibuprofen tablets.
Figure 31B:
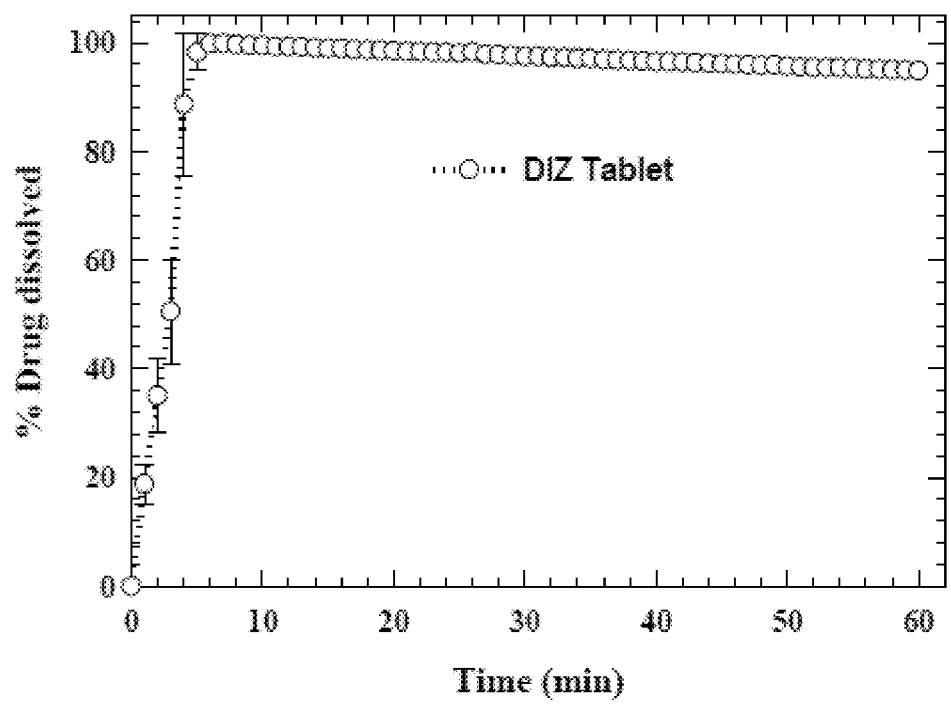
FIG. 31B illustrates the dissolution results for the manufactured diazepam tablets.

FIGS. 31A and 31B illustrate the dissolution results for the manufactured IBU and DIZ tablets, respectively. Average and standard deviation are depicted (n=6). According to USP monograph, 80% IBU should dissolve within 60 minutes, and 85% DIZ should dissolve within 30 minutes. The time it takes for 80% of the drug to dissolve ($t_{80}$) for IBU tablets and DIZ tablets is 23 minutes and 4 minutes, respectively. Hence, dissolution results of both drug tablets meet the USP monograph.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer to, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of producing an ingestible pharmaceutical composition, comprising:
   receiving, with a controller, instructions regarding a first tablet dosage and a second tablet dosage;
   dispensing a first amount of a solid active pharmaceutical ingredient from a first dispenser;
   dispensing a first amount of an excipient from a second dispenser;
   blending the first amount of the solid active pharmaceutical ingredient and the first amount of the excipient in a blender to form a first mixture;
   forming a first tablet from the first mixture;
   dispensing a second amount of the solid active pharmaceutical ingredient from the first dispenser;
   dispensing a second amount of the excipient from the second dispenser;
   blending the second amount of the solid active pharmaceutical ingredient and the second amount of the excipient in the blender to form a second mixture; and
   forming a second tablet from the second mixture,
   wherein the first dispenser, the second dispenser and the blender are coupled to a frame, and
   wherein the first amount of the solid active pharmaceutical ingredient and the first amount of the excipient are dispensed into a carriage.

2. The method of claim 1, further comprising:
   weighing the first amount of the solid active pharmaceutical ingredient and the first amount of the excipient; and
   weighing the second amount of the solid active pharmaceutical ingredient and the second amount of the excipient.

3. The method of claim 1, further comprising weighing, with a weigh scale, the first amount of the solid active pharmaceutical ingredient and the first amount of the excipient while the first amount of the solid active pharmaceutical ingredient and the first amount of the excipient are in the carriage, the carriage being coupled to the weigh scale.

4. The method of claim 1, further comprising conveying, with the carriage, the first amount of the solid active pharmaceutical ingredient and the first amount of the excipient to the blender.

5. The method of claim 1, further comprising dispensing a portion of the first mixture to form the first tablet.

6. The method of claim 5, further comprising compressing the portion of the first mixture to form the first tablet.

7. The method of claim 1, further comprising weighing the first tablet and weighing the second tablet.

8. The method of claim 3, further comprising tilting the carriage to cause the first amount of the solid active pharmaceutical ingredient and the first amount of the excipient to exit the carriage and enter the blender.

9. The method of claim 1, further comprising opening a portion of the blender to release the first mixture.

10. The method of claim 1, wherein instructions regarding the second tablet dosage are received at a different point in time than instructions regarding the first tablet dosage, and wherein the step of dispensing the second amount of the solid active pharmaceutical ingredient is in response to the instructions regarding the second tablet dosage.

11. The method of claim 1, wherein the second amount of the solid active pharmaceutical ingredient is different from the first amount of the solid active pharmaceutical ingredient.

12. The method of claim 1, wherein the second amount of the solid active pharmaceutical ingredient is the same as the first amount of the solid active pharmaceutical ingredient.

13. The method of claim 1, wherein the second amount of the excipient is different from the first amount of the excipient.

14. The method of claim 1, wherein the second amount of the excipient is the same as the first amount of the excipient.

15. The method of claim 1, further comprising:
   receiving, with a controller, instructions regarding a first drug type and a second drug type; and
   dispensing a second solid active pharmaceutical ingredient, the second solid active pharmaceutical ingredient being compositionally different from the solid active pharmaceutical ingredient.

16. A method of producing an ingestible pharmaceutical composition, comprising:

receiving, with a controller, instructions regarding a first drug type and a second drug type;

dispensing a first solid active pharmaceutical ingredient;

dispensing a first excipient;

blending the first solid active pharmaceutical ingredient and the first excipient to form a first mixture having a volume of less than 10 L;

forming a tablet from the first mixture;

dispensing a second solid active pharmaceutical ingredient, the second solid active pharmaceutical ingredient being compositionally different from the first solid active pharmaceutical ingredient;

dispensing a second excipient;

blending the second solid active pharmaceutical ingredient and the second excipient to form a second mixture; and forming a tablet from the second mixture, wherein the first solid active pharmaceutical ingredient and the first excipient are dispensed into a carriage.

17. The method of claim 16, further comprising:

weighing the first solid active pharmaceutical ingredient and the first excipient; and weighing the second solid active pharmaceutical ingredient and the second excipient.

18. The method of claim 16, further comprising weighing, with a weigh scale, the first solid active pharmaceutical ingredient and the first excipient while the first solid active pharmaceutical ingredient and the first excipient are in the carriage, the carriage being coupled to the weigh scale.

19. The method of claim 16, further comprising conveying, with the carriage, the first solid active pharmaceutical ingredient and the first excipient to a blender.

20. The method of claim 16, further comprising weighing the tablet from the first mixture and weighing the tablet from the second mixture.

21. The method of claim 16, wherein the first solid active pharmaceutical ingredient and the first excipient are dispensed from a plurality of dispensers and the blending is performed in a blender, the plurality of dispensers and the blender being coupled to a frame.

22. A system for producing an ingestible pharmaceutical composition, comprising:

a plurality of dispensers;

a first weigh scale configured to weigh material dispensed from the plurality of dispensers; and a blender configured to receive and mix the material dispensed from the plurality of dispensers to form a first mixture, the blender having a mixing vessel having a volume of less than 10 L; and a carriage configured to convey the material dispensed from the plurality of dispensers to the blender.

23. The system of claim 22, further comprising a secondary dispenser that is configured to receive the first mixture from the blender and dispenses discrete amounts of the first mixture.

24. The system of claim 23, wherein the secondary dispenser is configured to operate via a tapping mechanism.

25. The system of claim 22, further comprising a tableting unit including a tablet die and a tablet press that are configured to form a tablet from portions of the first mixture.

26. The system of claim 22, further comprising a tilt actuator configured to cause the carriage to tilt.

27. The system of claim 22, wherein the first weigh scale comprises a load cell.

28. The system of claim 25, further comprising a second weigh scale positioned to weigh tablets from the tableting unit.

29. The system of claim 22, further comprising a frame, wherein the plurality of dispensers and the first weigh scale are coupled to the frame.

* * * * *